(12) United States Patent
Sato et al.

(10) Patent No.: US 9,809,641 B2
(45) Date of Patent: Nov. 7, 2017

(54) LACTOFERRIN FUSION PROTEIN AND METHOD FOR PREPARATION THEREOF

(71) Applicant: NRL PHARMA, INC., Kawasaki-shi, Kanagawa (JP)

(72) Inventors: Atsushi Sato, Kanagawa (JP); Shinji Kagaya, Kanagawa (JP)

(73) Assignee: NRL PHARMA, INC., Kawasaki-shi, Kanagawa (JP)

( * ) Notice: Subject to any disclaimer, the term of this patent is extended or adjusted under 35 U.S.C. 154(b) by 165 days.

(21) Appl. No.: 14/395,826

(22) PCT Filed: Apr. 23, 2013

(86) PCT No.: PCT/JP2013/062685
§ 371 (c)(1),
(2) Date: Oct. 21, 2014

(87) PCT Pub. No.: WO2013/162050
PCT Pub. Date: Oct. 31, 2013

(65) Prior Publication Data
US 2015/0093382 A1   Apr. 2, 2015

(30) Foreign Application Priority Data
Apr. 23, 2012 (JP) ................. 2012-098085

(51) Int. Cl.
| | |
|---|---|
| C07K 14/79 | (2006.01) |
| C12N 15/62 | (2006.01) |
| C12N 15/82 | (2006.01) |
| A01K 67/027 | (2006.01) |
| A61K 38/00 | (2006.01) |

(52) U.S. Cl.
CPC .......... *C07K 14/79* (2013.01); *A01K 67/0275* (2013.01); *C12N 15/62* (2013.01); *C12N 15/8257* (2013.01); *A01K 2217/052* (2013.01); *A01K 2267/01* (2013.01); *A61K 38/00* (2013.01); *C07K 2319/30* (2013.01)

(58) Field of Classification Search
CPC ........ C07K 14/79; C12N 15/09; C12N 15/62; C12N 15/8257
See application file for complete search history.

(56) References Cited

U.S. PATENT DOCUMENTS

| | | | |
|---|---|---|---|
| 5,723,125 A | 3/1998 | Chang et al. | |
| 6,111,081 A * | 8/2000 | Conneely | C07K 14/79 435/252.3 |
| 6,423,509 B1 | 7/2002 | Sung et al. | |
| 6,660,843 B1 * | 12/2003 | Feige | C07K 14/505 530/350 |
| 7,148,321 B2 | 12/2006 | Gillies et al. | |
| 7,229,962 B2 | 6/2007 | Chung et al. | |
| 8,273,351 B2 | 9/2012 | TenHoor et al. | |

FOREIGN PATENT DOCUMENTS

| | | |
|---|---|---|
| EP | 1932855 A1 | 6/2008 |
| JP | 2000511424 A | 9/2000 |
| JP | 2002520045 A | 7/2002 |
| JP | 2003512011 A | 4/2003 |
| JP | 2004521655 A | 7/2004 |
| JP | 2007105044 A | 4/2007 |
| JP | 2008509153 A | 3/2008 |
| JP | 4234438 B2 | 3/2009 |
| JP | 2010514699 A | 5/2010 |
| JP | 2010531134 A | 9/2010 |
| JP | 2011523351 A | 8/2011 |
| WO | WO-2006017688 A2 | 2/2006 |
| WO | WO-2008080042 A2 | 7/2008 |
| WO | WO-2008147143 A2 | 12/2008 |

OTHER PUBLICATIONS

Mikayama et al. (1993) Proc. Natl. Acad. Sci. USA vol. 90, pp. 10056-10060.*
Voet et al. (1990) Biochemistry John Wiley & Sons, Inc., pp. 126-128 and 228-234.*
JP Application No. 2014-512737—Notice of Reasons for Rejection mailed Aug. 25, 2015.
Japanese Application No. 2014-51237—Office Action dated May 19, 2015 (with translation).
Jazayeri, et al., "FC-Based Cytokines—Prospects for Engineering Superior Therapeutics", Biodrugs, 2008 22, 11-26.
Yeung, et al., "Engineering Human IgG1 Affinity to Human Neonatal Fc Receptor: Impact of Affinity Improvement on Pharmacokinetics in Primates", J. Immunol., 2009, 182, 7663-7671.
Suzuki, et al., "Importance of Neonatal FcR in Regulating the Serum Half-Life of Therapeutic Proteins Containing the Fc Domain of Human IgG1: A Comparative Study of the Affinity of Monoclonal Antibodies and Fc-Fusion Proteins to Human Neonatal FcR", J. Immunol., 2010, 184, 1968-1976.
Batra, et al., "Insertion of Constant Region Domains of Human IgG1 into CD4-PE40 Increases its Plasma Half-Life", Mol Immunol., 1993, 30, 379-386.
Dimitrov, D.S., "Review-Engineered CH2 domains (nanoantibodies)", mAbs, 2009, 1, 26-28.

(Continued)

Primary Examiner — Prema Mertz
(74) Attorney, Agent, or Firm — Drinker Biddle & Reath LLP

(57) ABSTRACT

The present invention aims to provide a lactoferrin fusion protein, which is configured to retain the biological activities of natural lactoferrin, to have a significantly prolonged in vivo lifetime, and to be more clinically useful than natural and gene recombinant lactoferrin, as well as a method for preparation thereof, etc. The present invention provides a fusion protein formed with a protein or peptide comprising an FcRn-binding region and lactoferrin or a biologically active fragment or peptide of lactoferrin, which is represented by:

(LF-s-Y)n or (Y-s-LF)n

[wherein LF represents lactoferrin or a biologically active fragment or peptide of lactoferrin, represents the protein or peptide comprising an FcRn-binding region, s represents ally amino acid sequence of 0 to 10 residues, and n represents an integer of 1 to 10], or a variant thereof.

6 Claims, 28 Drawing Sheets

(56) References Cited

OTHER PUBLICATIONS

Gong, et al., "Shortened Engineered Human Antibody CH2 Domains: Increased Stability and Binding to the Human Neonatal Receptor", J. Biol. Chem., 2011, 286, 27288-27293.
PCT/2013/062685—International Search Report dated Jul. 16, 2013.
EP Application No. 13780579.2—Extended European Search Report dated Dec. 15, 2015.
Jan Terje Andersen, et al., "Extending Half-life by Indirect Targeting of the Neonatel Fc Receptor (FcRn) Using a Minimal Albumin Binding Domain", The Journal of Biological Chemistry, Feb. 18, 2011, vol. 286, No. 7, pp. 5234-5241.
Se Jin Im, et al., "Natural Form of Noncytolytic Flexible Human Fc as a Long-Acting Carrier of Agnostic Ligand, Erythropoietin", Sep. 2011, PLoS ONE 6(9), e24574.

\* cited by examiner

Figure 17A

MKLVFLVLLFLGALGLCLAGRRRRSVQWCAVSQPEATKCFQWQRNMRK
VRGPPVSCIKRDSPIQCIQAIAENRADAVTLDGGFIYEAGLAPYKLRPVAA
EVYGTERQPRTHYYAVAVVKKGGSFQLNELQGLKSCHTGLRRTAGWNVP
IGTLRPFLNWTGPPEPIEAAVARFFSASCVPGADKGQFPNLCRLCAGTGE
NKCAFSSQEPYFSYSGAFKCLRDGAGDVAFIRESTVFEDLSDEAERDEYE
LLCPDNTRKPVDKFKDCHLARVPSHAVVARSVNGKEDAIWNLLRQAQE
KFGKDKSPKFQLFGSPSGQKDLLFKDSAIGFSRVPPRIDSGLYLGSGYFT
AIQNLRKSEEEVAARRARVVWCAVGEQELRKCNQWSGLSEGSVTCSSAS
TTEDCIALVLKGEADAMSLDGGYVYTAGKCGLVPVLAENYKSQQSSDPD
PNCVDRPVEGYLAVAVVRRSDTSLTWNSVKGKKSCHTAVDRTAGWNIPM
GLLFNQTGSCKFDEYFSQSCAPGSDPRSNLCALCIGDEQGENKCVPNSN
ERYYGYTGAFRCLAENAGDVAFVKDVTVLQNTDGNNNEAWAKDLKLAD
FALLCLDGKRKPVTEARSCHLAMAPNHAVVSRMDKVERLKQVLLHQQA
KFGRNGSDCPDKFCLFQSETKNLLFNDNTECLARLHGKTTYEKYLGPQ
YVAGITNLKKCSTSPLLEACEFLRK<u>DPE</u>*EPKSCDKTHTCPPCP*<u>APELLGG
PSVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEKT
ISKAK</u>GQPREPQVYTLPPSRDELTKNQVSLTCLVKGFYPSDIAVEWESNG
QPENNYKTTPPVLDSDGSFFLYSKLTVDKSRWQQGNVFSCSVMHEALH
NHYTQKSLSLSPGK

Figure 17B

MKLVFLVLLFLGALGLCLAGRRRRSVQWCAVSQPEATKCFQWQRNMRK
VRGPPVSCIKRDSPIQCIQAIAENRADAVTLDGGFIYEAGLAPYKLRPVAA
EVYGTERQPRTHYYAVAVVKKGGSFQLNELQGLKSCHTGLRRTAGWNVP
IGTLRPFLNWTGPPEPIEAAVARFFSASCVPGADKGQFPNLCRLCAGTGE
NKCAFSSQEPYFSYSGAFKCLRDGAGDVAFIRESTVFEDLSDEAERDEYE
LLCPDNTRKPVDKFKDCHLARVPSHAVVARSVNGKEDAIWNLLRQAQE
KFGKDKSPKFQLFGSPSGQKDLLFKDSAIGFSRVPPRIDSGLYLGSGYFT
AIQNLRKSEEEVAARRARVVWCAVGEQELRKCNQWSGLSEGSVTCSSAS
TTEDCIALVLKGEADAMSLDGGYVYTAGKCGLVPVLAENYKSQQSSDPD
PNCVDRPVEGYLAVAVVRRSDTSLTWNSVKGKKSCHTAVDRTAGWNIPM
GLLFNQTGSCKFDEYFSQSCAPGSDPRSNLCALCIGDEQGENKCVPNSN
ERYYGYTGAFRCLAENAGDVAFVKDVTVLQNTDGNNNEAWAKDLKLAD
FALLCLDGKRKPVTEARSCHLAMAPNHAVVSRMDKVERLKQVLLHQQA
KFGRNGSDCPDKFCLFQSETKNLLFNDNTECLARLHGKTTYEKYLGPQ
YVAGITNLKKCSTSPLLEACEFLRK<u>DPAPELLGGPSVFLFPPKPKDTLMI
SRTPEVTCVVVDVSHEDPEVKFNWYVDGVEVHNAKTKPREEQYNSTYR
VVSVLTVLHQDWLNGKEYKCKVSNKALPAPIEKTISKAK</u>GQPREPQVYT
LPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

SEQUENCE LISTING

<160> NUMBER OF SEQ ID NOS: 6

<210> SEQ ID NO 1
<211> LENGTH: 27
<212> TYPE: DNA
<213> ORGANISM: Artificial Sequence
<220> FEATURE:
<223> OTHER INFORMATION: primer  S_LFex_XhoI_ATG

<400> SEQUENCE: 1
ctcgagatga aacttgtctt cctcgtc                                              27

<210> SEQ ID NO 2
<211> LENGTH: 26
<212> TYPE: DNA
<213> ORGANISM: Artificial Sequence
<220> FEATURE:
<223> OTHER INFORMATION: primer  AS_LFex_TAA _XbaI

<400> SEQUENCE: 2
tctagattac ttcctgagga attcac                                               26

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
aattcctcag gaaggatcct                                                      20

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
ctagaggatc cttcctgagg                                                      20

<210> SEQ ID NO 5
<211> LENGTH: 946
<212> TYPE: PRT
<213> ORGANISM: Artificial Sequence
<220> FEATURE:
<223> OTHER INFORMATION: hLF-hFc (Hinge-CH2-CH3)

<400> SEQUENCE: 5

Met Lys Leu Val Phe Leu Val Leu Leu Phe Leu Gly Ala Leu Gly Leu
1               5                   10                  15

Cys Leu Ala Gly Arg Arg Arg Arg Ser Val Gln Trp Cys Ala Val Ser
            20                  25                  30

Gln Pro Glu Ala Thr Lys Cys Phe Gln Trp Gln Arg Asn Met Arg Lys
        35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr

-continued

```
                100                 105                 110
Tyr Ala Val Ala Val Lys Lys Gly Gly Ser Phe Gln Leu Asn Glu
            115                 120                 125

Leu Gln Gly Leu Lys Ser Cys His Thr Gly Leu Arg Arg Thr Ala Gly
        130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
        195                 200                 205

Tyr Phe Ser Tyr Ser Gly Ala Phe Lys Cys Leu Arg Asp Gly Ala Gly
    210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
        275                 280                 285

Asn Leu Leu Arg Gln Ala Gln Glu Lys Phe Gly Lys Asp Lys Ser Pro
    290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gln Asn Leu Arg
            340                 345                 350

Lys Ser Glu Glu Glu Val Ala Ala Arg Arg Ala Arg Val Val Trp Cys
        355                 360                 365

Ala Val Gly Glu Gln Glu Leu Arg Lys Cys Asn Gln Trp Ser Gly Leu
    370                 375                 380

Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Gly
                405                 410                 415

Gly Tyr Val Tyr Thr Ala Gly Lys Cys Gly Leu Val Pro Val Leu Ala
            420                 425                 430

Glu Asn Tyr Lys Ser Gln Gln Ser Ser Asp Pro Asp Pro Asn Cys Val
        435                 440                 445

Asp Arg Pro Val Glu Gly Tyr Leu Ala Val Ala Val Val Arg Arg Ser
    450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
                485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
        515                 520                 525
```

```
Gly Asp Glu Gln Gly Glu Asn Lys Cys Val Pro Asn Ser Asn Glu Arg
    530                 535                 540

Tyr Tyr Gly Tyr Thr Gly Ala Phe Arg Cys Leu Ala Glu Asn Ala Gly
545                 550                 555                 560

Asp Val Ala Phe Val Lys Asp Val Thr Val Leu Gln Asn Thr Asp Gly
                565                 570                 575

Asn Asn Asn Glu Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Val Ser Arg Met Asp
    610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
        675                 680                 685

Ala Gly Ile Thr Asn Leu Lys Lys Cys Ser Thr Ser Pro Leu Leu Glu
    690                 695                 700

Ala Cys Glu Phe Leu Arg Lys Asp Pro Glu Glu Pro Lys Ser Cys Asp
705                 710                 715                 720

Lys Thr His Thr Cys Pro Pro Cys Pro Ala Pro Glu Leu Leu Gly Gly
                725                 730                 735

Pro Ser Val Phe Leu Phe Pro Pro Lys Pro Lys Asp Thr Leu Met Ile
            740                 745                 750

Ser Arg Thr Pro Glu Val Thr Cys Val Val Val Asp Val Ser His Glu
        755                 760                 765

Asp Pro Glu Val Lys Phe Asn Trp Tyr Val Asp Gly Val Glu Val His
    770                 775                 780

Asn Ala Lys Thr Lys Pro Arg Glu Glu Gln Tyr Asn Ser Thr Tyr Arg
785                 790                 795                 800

Val Val Ser Val Leu Thr Val Leu His Gln Asp Trp Leu Asn Gly Lys
                805                 810                 815

Glu Tyr Lys Cys Lys Val Ser Asn Lys Ala Leu Pro Ala Pro Ile Glu
            820                 825                 830

Lys Thr Ile Ser Lys Ala Lys Gly Gln Pro Arg Glu Pro Gln Val Tyr
        835                 840                 845

Thr Leu Pro Pro Ser Arg Asp Glu Leu Thr Lys Asn Gln Val Ser Leu
    850                 855                 860

Thr Cys Leu Val Lys Gly Phe Tyr Pro Ser Asp Ile Ala Val Glu Trp
865                 870                 875                 880

Glu Ser Asn Gly Gln Pro Glu Asn Asn Tyr Lys Thr Thr Pro Pro Val
                885                 890                 895

Leu Asp Ser Asp Gly Ser Phe Phe Leu Tyr Ser Lys Leu Thr Val Asp
            900                 905                 910

Lys Ser Arg Trp Gln Gln Gly Asn Val Phe Ser Cys Ser Val Met His
        915                 920                 925

Glu Ala Leu His Asn His Tyr Thr Gln Lys Ser Leu Ser Leu Ser Pro
    930                 935                 940
```

-continued

Gly Lys
945

<210> SEQ ID NO 6
<211> LENGTH: 930
<212> TYPE: PRT
<213> ORGANISM: Artificial Sequence
<220> FEATURE:
<223> OTHER INFORMATION: hLF-hFc (CH2-CH3)

<400> SEQUENCE: 6

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser
            20                  25                  30

Gln Pro Glu Ala Thr Lys Cys Phe Gln Trp Gln Arg Asn Met Arg Lys
        35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
        115                 120                 125

Leu Gln Gly Leu Lys Ser Cys His Thr Gly Leu Arg Arg Thr Ala Gly
    130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
        195                 200                 205

Tyr Phe Ser Tyr Ser Gly Ala Phe Lys Cys Leu Arg Asp Gly Ala Gly
    210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
        275                 280                 285

Asn Leu Leu Arg Gln Ala Gln Glu Lys Phe Gly Lys Asp Lys Ser Pro
    290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gly Asn Leu Arg
            340                 345                 350

-continued

```
Lys Ser Glu Glu Val Ala Ala Arg Arg Ala Arg Val Val Trp Cys
            355                 360                 365
Ala Val Gly Glu Gln Glu Leu Arg Lys Cys Asn Gln Trp Ser Gly Leu
        370                 375                 380
Ser Glu Gly Ser Val Thr Cys Ser Ser Ala Ser Thr Thr Glu Asp Cys
385                 390                 395                 400
Ile Ala Leu Val Leu Lys Gly Glu Ala Asp Ala Met Ser Leu Asp Gly
                405                 410                 415
Gly Tyr Val Tyr Thr Ala Gly Lys Cys Gly Leu Val Pro Val Leu Ala
            420                 425                 430
Glu Asn Tyr Lys Ser Gln Gln Ser Ser Asp Pro Asp Pro Asn Cys Val
        435                 440                 445
Asp Arg Pro Val Glu Gly Tyr Leu Ala Val Ala Val Val Arg Arg Ser
    450                 455                 460
Asp Thr Ser Leu Thr Trp Asn Ser Val Lys Gly Lys Lys Ser Cys His
465                 470                 475                 480
Thr Ala Val Asp Arg Thr Ala Gly Trp Asn Ile Pro Met Gly Leu Leu
                485                 490                 495
Phe Asn Gln Thr Gly Ser Cys Lys Phe Asp Glu Tyr Phe Ser Gln Ser
            500                 505                 510
Cys Ala Pro Gly Ser Asp Pro Arg Ser Asn Leu Cys Ala Leu Cys Ile
        515                 520                 525
Gly Asp Glu Gln Gly Glu Asn Lys Cys Val Pro Asn Ser Asn Glu Arg
    530                 535                 540
Tyr Tyr Gly Tyr Thr Gly Ala Phe Arg Cys Leu Ala Glu Asn Ala Gly
545                 550                 555                 560
Asp Val Ala Phe Val Lys Asp Val Thr Val Leu Gln Asn Thr Asp Gly
                565                 570                 575
Asn Asn Asn Glu Ala Trp Ala Lys Asp Leu Lys Leu Ala Asp Phe Ala
            580                 585                 590
Leu Leu Cys Leu Asp Gly Lys Arg Lys Pro Val Thr Glu Ala Arg Ser
        595                 600                 605
Cys His Leu Ala Met Ala Pro Asn His Ala Val Val Ser Arg Met Asp
    610                 615                 620
Lys Val Glu Arg Leu Lys Gln Val Leu Leu His Gln Gln Ala Lys Phe
625                 630                 635                 640
Gly Arg Asn Gly Ser Asp Cys Pro Asp Lys Phe Cys Leu Phe Gln Ser
                645                 650                 655
Glu Thr Lys Asn Leu Leu Phe Asn Asp Asn Thr Glu Cys Leu Ala Arg
            660                 665                 670
Leu His Gly Lys Thr Thr Tyr Glu Lys Tyr Leu Gly Pro Gln Tyr Val
        675                 680                 685
Ala Gly Ile Thr Asn Leu Lys Lys Cys Ser Thr Ser Pro Leu Leu Glu
    690                 695                 700
Ala Cys Glu Phe Leu Arg Lys Asp Pro Ala Pro Glu Leu Leu Gly Gly
705                 710                 715                 720
Pro Ser Val Phe Leu Phe Pro Lys Pro Lys Asp Thr Leu Met Ile
                725                 730                 735
Ser Arg Thr Pro Glu Val Thr Cys Val Val Asp Val Ser His Glu
            740                 745                 750
Asp Pro Glu Val Lys Phe Asn Trp Tyr Val Asp Gly Val Glu Val His
        755                 760                 765
Asn Ala Lys Thr Lys Pro Arg Glu Glu Gln Tyr Asn Ser Thr Tyr Arg
```

```
                770                 775                 780
Val Val Ser Val Leu Thr Val Leu His Gln Asp Trp Leu Asn Gly Lys
785                 790                 795                 800

Glu Tyr Lys Cys Lys Val Ser Asn Lys Ala Leu Pro Ala Pro Ile Glu
                805                 810                 815

Lys Thr Ile Ser Lys Ala Lys Gly Gln Pro Arg Glu Pro Gln Val Tyr
                820                 825                 830

Thr Leu Pro Pro Ser Arg Asp Glu Leu Thr Lys Asn Gln Val Ser Leu
                835                 840                 845

Thr Cys Leu Val Lys Gly Phe Tyr Pro Ser Asp Ile Ala Val Glu Trp
                850                 855                 860

Glu Ser Asn Gly Gln Pro Glu Asn Asn Tyr Lys Thr Thr Pro Pro Val
865                 870                 875                 880

Leu Asp Ser Asp Gly Ser Phe Phe Leu Tyr Ser Lys Leu Thr Val Asp
                885                 890                 895

Lys Ser Arg Trp Gln Gln Gly Asn Val Phe Ser Cys Ser Val Met His
                900                 905                 910

Glu Ala Leu His Asn His Tyr Thr Gln Lys Ser Leu Ser Leu Ser Pro
                915                 920                 925

Gly Lys
930
```

LACTOFERRIN FUSION PROTEIN AND METHOD FOR PREPARATION THEREOF

CROSS REFERENCE TO RELATED APPLICATIONS

This application is the National Stage of International Application No. PCT/JP2013/062685, filed Apr. 23, 2013, and claims benefit of Japanese Application No. 2012-098085 filed on Apr. 23, 2012.

REFERENCE TO A SEQUENCE LISTING

The instant application contains a sequence listing which has been submitted in ASCII format via EFS-Web and is hereby incorporated by reference in its entirety. Said ASCII copy, created on Oct. 14, 2014, is named G1177_Seq_Listing.txt and is 17,222 bytes in size.

TECHNICAL FIELD

The present invention relates to a lactoferrin fusion protein having improved properties, uses thereof and a method for preparation thereof.

BACKGROUND

Lactoferrin is a glycoprotein having a molecular weight of about 80,000, which occurs mainly in mammalian milk and is also found in neutrophils, tears, saliva, nasal discharge, bile, semen, etc. Because of its iron-binding ability, lactoferrin belongs to the transferrin family. Known physiological activities of lactoferrin include an antibacterial effect, an iron metabolism regulatory effect, a cell proliferation promotion effect, a hematopoietic effect, an anti-inflammatory effect, an antioxidative effect, a phagocytosis enhancement effect, an antiviral effect, a bifidobacteria growth promotion effect, an anticancer effect, a cancer metastasis inhibitory effect, a translocation inhibitory effect and so on. Further, recent studies have indicated that lactoferrin also has a lipid metabolism improvement effect, an analgesic or anti-stress effect, and an anti-aging effect. As described above, lactoferrin is a multifunctional physiologically active protein having a wide range of functions and is therefore expected for use in, e.g., pharmaceutical and/or food applications for the purpose of restoration or promotion of health. Food products containing lactoferrin have already been commercially available.

When given orally, lactoferrin will be hydrolyzed by the action of pepsin, an acidic protease contained in the gastric juice, and then cleaved into peptides. For this reason, lactoferrin molecules are almost unable to reach the intestinal tract. However, lactoferrin receptors are known to be present on the small intestinal mucosa in the case of the digestive tract, and recent studies have indicated that lactoferrin is taken into the body through the intestinal tract and exerts its biological activities. Thus, for exertion of the lactoferrin's biological activities, it is important to ensure that lactoferrin is allowed to reach the intestinal tract without being hydrolyzed by the action of pepsin in the gastric juice. Moreover, when formulated into injections, lactoferrin will be exposed to cleavage catalyzed by proteases (e.g., chymotrypsin, elastase) contained in tissues and organs, so that it is practically important to impart resistance against these proteases for the purpose of increasing the in vivo stability in tissues and organs where lactoferrin is administered.

IgG antibodies are known to have a long half-life in blood because they are prevented from being cleaved in vivo through a recycling mechanism mediated by the neonatal Fc receptor (hereinafter referred to as "FcRn"). In addition, antibody drugs, whose targets are limited to specific proteins or peptides or the like and whose mechanisms of action are therefore limited, are regarded as having fewer side effects than conventional synthetic compounds.

The concept of biological formulations based on fusion proteins with IgG antibody or its Fc region has been known per se. By way of example, as an agent for suppressing acute graft rejection following renal transplantation, a CD3-targeting antibody drug was approved in 1986 and has been used over a long period of time.

However, in general, fusion proteins are often observed to have reduced biological activities when compared to non-fused proteins. This is because their active sites have been affected as a result of fusion. By way of example, when compared to endogenous TPO, TPOR-binding mimetic peptides were found to be comparable in terms of TPOR-binding levels, but tended to have slightly lower biological activities when tested in vitro.

Furthermore, in the case of a fusion protein formed with IFN-α and Fc region, which is designed to increase the half-life of IFN-α in blood, the half-life in blood has been greatly increased but there arises a disadvantage in that the physiological activities of IFN-α are reduced. Thus, with regard to conditions and others required for preparation of fusion proteins having desired properties, sufficient studies should be conducted for each protein.

PRIOR ART DOCUMENTS

Patent Documents

Patent Document 1: JP 2007-105044 A
Patent Document 2: Japanese Patent No. 4234438
Patent Document 3: JP 2011-523351 A
Patent Document 4: JP 2004-521655 A
Patent Document 5: U.S. Pat. No. 5,723,125

Non-Patent Documents

Non-patent Document 1: Jazayeri, J. A. et al., Biodrugs, 22, 11-26 (2008)
Non-patent Document 2: Yeung, Y. A. et al., J. Immunol., 182, 7663-7671 (2009)
Non-patent Document 3: Suzuki, T. et al., J. Immunol., 184, 1968-1976 (2010)
Non-patent Document 4: Batra, J. K., et al., Mol. Immunol., 30, 379-386, (1993)
Non-patent Document 5: Dimitrov, D. S., mAbs, 1, 26-28 (2009)
Non-patent Document 6: Gong, R. et al., J. Biol. Chem., 286, 27288-27293 (2011)

DISCLOSURE OF THE INVENTION

The present invention aims to provide a highly clinically useful lactoferrin fusion protein, which is configured to have reduced antigenicity, to be resistant against proteases, to allow oral, tissue and/or organ administration, and to have a prolonged in vivo life time, as well as a method for preparation thereof. More specifically, the present invention aims to provide a lactoferrin fusion protein, which is configured to retain the biological activities of naturally occurring lactoferrin, to have a significantly prolonged in vivo life time, and to be more clinically useful than naturally occurring lactoferrin and gene recombinant lactoferrin, as well as a method for preparation thereof, etc.

As a result of extensive and intensive efforts made to design lactoferrin having a higher order structure comparable to that of the naturally occurring form, wherein its physiological activities are not impaired and a long half-life is maintained, the inventors of the present invention have found that when lactoferrin protein was fused with an FcRn-binding protein (Fc region) and examined for its stability in blood, the lactoferrin protein fused with the Fc region showed a significant 5.4-fold increase in its half-life when compared to the non-fused control. Moreover, from the results of CD spectra and iron-binding ability measurement, the inventors of the present invention have found unexpected results that the fusion protein showed no change in the three-dimensional structure of lactoferrin per se upon fusion with the Fc region, and in terms of heat stability, the three-dimensional structure is maintained at a temperature of at least 30° C. or higher, even at 65° C. or higher, and the biological activities are also not impaired at all. Furthermore, the inventors of the present invention have obtained the results that the prepared lactoferrin fusion protein has resistance against proteases and also retains the iron-chelating ability, which is the most important biological activity. These findings led to the completion of the present invention.

Namely, the present invention provides the following.

[1] A fusion protein formed with lactoferrin and a protein or peptide comprising an FcRn-binding region, which is represented by:

(LF-s-Y)n or (Y-s-LF)n

[wherein LF represents lactoferrin or a biologically active fragment or peptide of lactoferrin, Y represents the protein or peptide comprising an FcRn-binding region, s represents any amino acid sequence of 0 to 10 residues, and n represents an integer of 1 to 10], or a variant thereof.

[2] The fusion protein or variant thereof according to [1] above, wherein the protein or peptide comprising an FcRn-binding region comprises any of IgG, the heavy chain of IgG, the heavy chain Fc region of IgG; the CH2 and CH3 domains of the Fc region, the CH2 domain of the Fc region, albumin and the FcRn-binding region of albumin.

[3] The fusion protein or variant thereof according to [1] or [2] above, wherein the fusion protein is a monomer or dimer (n=1 or 2).

[4] The fusion protein or variant thereof according to [1] or [2] above, wherein the fusion protein is a monomer.

[5] The fusion protein or variant thereof according to any one of [1] to [4] above, wherein the fusion protein retains 50% or more of the iron-chelating ability of natural or gene recombinant lactoferrin.

[6] The fusion protein or variant thereof according to any one of [I] to [5] above, wherein the fusion protein is taken up via the lactoferrin receptor or/and the IgG/albumin receptor.

[7] The fusion protein or variant thereof according to any one of [1] to [6] above, wherein the fusion protein has improved chymotrypsin resistance when compared to natural or gene recombinant lactoferrin.

[8] A nucleic acid molecule encoding the fusion protein or variant thereof according to any one of [1] to [7] above.

[9] An expression vector comprising the nucleic acid molecule according to [8] above.

[10] A host cell comprising the expression vector according to [9] above.

[11] A genetically modified non-human animal comprising the nucleic acid molecule according to [8] above.

[12] A genetically modified plant comprising the nucleic acid molecule according to [8] above.

[13] A therapeutic agent for diseases ameliorated by lactoferrin, which comprises the fusion protein or variant thereof according to any one of [1] to [7] above.

[14] A pharmaceutical composition comprising the fusion protein or variant thereof according to any one of [α] to [7] above and a carrier.

[15] A method for preparing the fusion protein or variant thereof according to any one of [1] to [7] above, which comprises culturing a host cell comprising a gene encoding the fusion protein or variant thereof to express the fusion protein or variant thereof, and collecting the fusion protein or variant thereof from the host cell or the medium thereof.

The fusion protein of the present invention or a variant thereof (hereinafter may also be referred to as "the fusion protein or the like") retains the iron-binding ability of lactoferrin, and therefore at least retains the important biological activities of lactoferrin, which are based on the iron-binding ability. Moreover, because of having a prolonged in vivo life time and resistance against proteases, the fusion protein or the like can exert its biological activities in vivo over a long period of time. Further, by being configured in the form of a fusion protein, it is less likely to be digested and cleaved with pepsin in the stomach and is therefore able to fully reach the intestine without requiring any additional pharmaceutical treatment for enteric purposes.

In addition, by being prepared through gene recombination technology, the fusion protein or the like of the present invention is also advantageous in terms of manufacturing control and quality control, and hence is particularly suitable for use as a pharmaceutical ingredient. Namely, such a fusion protein or the like and a method for preparation thereof according to the present invention enable the provision of lactoferrin in a more useful form as a pharmaceutical ingredient. Since lactoferrin is extremely safe and has a wide range of biological activities, the present invention allows more advantageous application of lactoferrin as a therapeutic or prophylactic agent for diseases or symptoms for which no effective therapeutic agent has been available. For example, application of lactoferrin can be widened to lifestyle-related diseases (e.g., arteriosclerosis, hypercholesterolemia, hyperlipidemia, hypertension, diabetes, fatty liver), cancers (e.g., prevention of carcinogenesis, secondary prevention of cancers, suppression of metastasis, enhanced effects of carcinostatic agents), autoimmune diseases (e.g., dry eye and dry mouth associated with Sjogren's syndrome, rheumatic arthritis, malignant rheumatoid arthritis, collagenosis, multiple sclerosis, systemic lupus erythematosus, systemic lupus erythematosus), psychoneurotic diseases (e.g., dementia, Alzheimer's disease, Parkinson's disease, epilepsy, depression, withdrawal, schizophrenia, various stress-induced diseases, menopausal symptoms), pain relief (e.g., enhancement of opioids such as morphine, cancer pain, neuropathic pain, post-herpetic pain, fibromyalgia, postoperative pain, glossodynia, menstrual pain, toothache, arthralgia, climacteric symptoms), hepatitis (e.g., various types of virus hepatitis, nonalcoholic hepatitis, cirrhosis), inflammatory bowel diseases (e.g., ulcerative colitis, Crohn's disease), irritable bowel syndrome, benign prostatic hyperplasia, frequent urination, insomnia, constipation and so on. Further, since lactoferrin has an antibacterial or antiviral effect and an immunostimulatory effect, the fusion protein of the present invention or a pharmaceutical composition comprising the same can also be applied to various types of infections and their associated inflammation, as exemplified by gastric mucosal infection with *Helicobacter pylori*, periodontal disease, pyorrhea alveolaris, ozostomia, oral candidiasis, stomatitis, angular cheilitis, rhinitis, esophagitis, cholecystitis, urinary tract infections, vaginal infections, tinea pedis, acne, infections with viruses of the herpes group, senile pneumonia, postoperative infections and so on, and it also has the effect of enhancing the action of antibiotics. On the other hand, lactoferrin also acts to provide immunological tolerance, and hence the fusion protein of the present invention or a pharmaceutical composition comprising the same can also be applied to allergic diseases such as pollinosis, atopic dermatitis, seborrhea, urticaria and so on. Notably, lactoferrin has a strong anti-oxidative stress effect based on its iron-chelating effect, and hence the fusion protein of the present invention or a pharmaceutical composition comprising the same can also be applied not only to Wilson's disease, fulminant hepatitis and so on, but also to anti-aging and rejuvenation effects on the skin and eyes, age-related macular degeneration, diabetic retinopathy, anti-keratinization and rejuvenation effects on mucosal epithelial cells, etc.

Moreover, the fusion protein of the present invention is taken up into cells via at least one receptor selected from the group consisting of the lactoferrin receptors, the IgG receptors and the albumin receptors, and therefore can be expected to have lower side effects.

BRIEF DESCRIPTION OF THE DRAWINGS

FIG. 12-B shows the secondary structure homology of hLF and the hinge-deficient and hinge-added hLF/hIgGFc fusion proteins. Panel B shows the CD spectrum obtained for the hinge-deficient fusion protein hLF/mhIgGFc.

FIG. 12-C shows the secondary structure homology of hLF and the hinge-deficient and hinge-added hLF/hIgGFc fusion proteins. Panel C shows the CD spectrum obtained for the hinge-added fusion protein d(hLF/hIgGFc).

FIG. 13-B shows the heat stability of hLF and the hinge-deficient and hinge-added hLF/hIgGFc fusion proteins. Panel B shows the CD spectrum obtained for the hinge-deficient fusion protein hLF/mhIgGFc.

FIG. 13-C shows the heat stability of hLF and the hinge-deficient and hinge-added hLF/hIgGFc fusion proteins. Panel C shows the CD spectrum obtained for the hinge-added fusion protein d(hLF/hIgGFc).

FIG. 15-B shows a schematic view of the hinge-added hLF/hIgGFc fusion protein, along with its cleavage site.

FIG. 17-A shows the amino acid sequence (SEQ ID NO: 5 in the Sequence Listing) of the human lactoferrin (hLF)/human IgG Fc fusion protein encoded by expression vector pOptiVEC/hLF-dFc. The double-lined section represents a sequence of spacer amino acids, the italic section represents a sequence of amino acids in the hinge region, the underlined bold section represents a sequence of amino acids in the CH2 domain, and the bold section represents a sequence of amino acids in the CH3 domain.

FIG. 17-B shows the amino acid sequence (SEQ ID NO: 6 in the Sequence Listing) of the hLF/hIgGFc fusion protein encoded by expression vector pOptiVEC/hLF-mFc. The double-lined section represents a sequence of spacer amino acids, the underlined bold section represents a sequence of amino acids in the CH2 domain, and the bold section represents a sequence of amino acids in the CH3 domain.

BEST MODES FOR CARRYING OUT THE INVENTION

Figure 1:
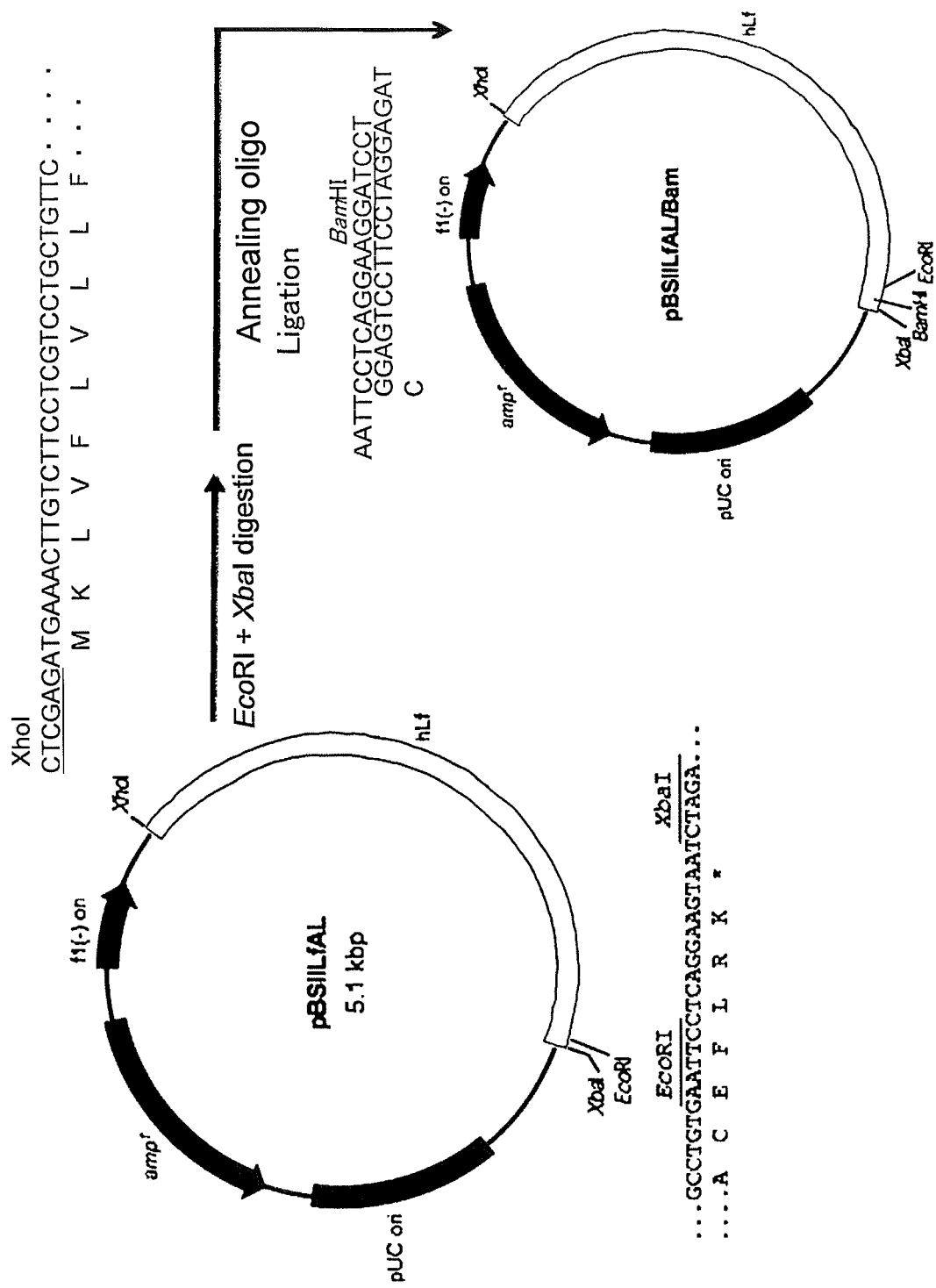
FIG. 1 shows a schematic representation where a synthetic oligonucleotide comprising a BamHI site is inserted into vector pBSIILfAL comprising the full-length human lactoferrin (hLF) cDNA to thereby prepare pBSIILfAL/Bam.

The present invention will be described in more detail below. The following embodiments are illustrated to describe the present invention, and it is not intended to limit the present invention only to these embodiments. The present invention can be implemented in various modes, without departing from the spirit of the present invention.

It should be noted that all publications cited herein, including prior art documents, patent gazettes and other patent documents, are incorporated herein by reference. Moreover, this specification incorporates the contents disclosed in the specification and drawings of Japanese Patent Application No. 2012-098085 (filed on Apr. 23, 2012), based on which the present application claims priority.

The fusion protein of the present invention is a biologically active fusion protein formed with a protein or peptide comprising an FcRn-binding region and lactoferrin or a biologically active fragment or peptide of lactoferrin. In the fusion protein of the present invention, such a protein or peptide to be linked with lactoferrin or a biologically active fragment or peptide of lactoferrin generally refers to a protein or peptide comprising a sequence known to bind to FcRn, and any protein or peptide may be used for this purpose as long as it is biocompatible or pharmacologically inert. For example, IgG or albumin, which is a blood component protein, is known to bind to FcRn. Thus, examples of the protein or peptide comprising an FcRn-binding region to be used in the present invention include those comprising IgG (IgG1, IgG2, IgG3, IgG4, IgG5, IgG6, IgG7), the heavy chain of IgG the Fc region in the heavy chain of IgG, the CH2 and CH3 domains of the Fc region, the CH2 domain, albumin, and the FcRn-binding region of albumin. The amino acid sequences of these proteins and peptides are known, and for use in the present invention, they may be the same as their naturally occurring sequences or may have a mutation(s).

Preferably, the protein or peptide comprising an FcRn-binding region to be used in the present invention should be resistant to cleavage from the state fused with lactoferrin. For example, when using an IgG Fc region including a hinge region, the hinge region forms disulfide linkages to thereby form a fusion protein in a dimeric form. However, the hinge region is highly susceptible to proteases. For this reason, it is possible to use an IgG Fc region which is free from the hinge region or has been modified to replace cysteine in the hinge region with another amino acid or to change the position of cysteine. Alternatively, the hinge region may be replaced with a different isotype-derived hinge region containing a glycosylation site to thereby enhance protease resistance by the presence of sugar chains (Patent Document 2). These embodiments also fall within the protein or peptide comprising an FcRn-binding region.

To prevent protease-catalyzed cleavage of the hinge region, a preferred strategy is to delete the hinge region to thereby prepare a hinge-deficient fusion protein. Because of having no hinge region, this fusion protein would have reduced binding to Fcy receptors or complements responsible for effector functions, and is therefore advantageous over a fusion protein having the hinge region (e.g., a hinge-added fusion protein) in terms of reducing cell damage cytotoxicity mediated by effector functions which leads to side effects and/or reducing activation of immunereaction mediated by effector functions which leads to elimination of the fusion protein from blood.

Such a protein or peptide comprising an FcRn-binding region may comprise other sequences in addition to the FcRn-binding region. For example, upon addition of a sequence covering the J chain which forms a multimer (e.g., IgA, IgM), higher-order multimerization is possible.

In the fusion protein, lactoferrin or a biologically active fragment or peptide of lactoferrin and the protein or peptide comprising an FcRn-binding region may be located such that either of them may be located at the N-terminal or C-terminal side of the other, although it is preferred that lactoferrin or a biologically active fragment or peptide of lactoferrin is located at the N-terminal side, while the protein or peptide comprising an FcRn-binding region is located at the C-terminal side. Thus, the fusion protein of the present invention is preferably represented by (LF-Y)n and/or the formula appearing in [1] above, wherein n=1 or 2, and more preferably represented by (LF-Y)n, wherein n=1. It should be noted that an additional sequence may be present between LF and Y, as described later.

"Lactoferrin" (LF) or a biologically active fragment or peptide of lactoferrin to be used in the fusion protein or the like of the present invention is gene recombinant lactoferrin (including a variant whose amino acids are partially substituted), and there is no limitation either on the type of organism from which the sequence used is derived or on the presence or absence of a modification(s). For example, the lactoferrin intended here may have the same amino acid sequence as natural lactoferrin obtained from humans and various animals (e.g., cow, horse, pig, sheep, goat, camel) or may comprise partial deletion, addition or substitution of amino acids as long as it has the desired physiological activities of lactoferrin. Various candidates are known for such a functional (biologically active) fragment or peptide of lactoferrin (see, e.g., "Programs and Abstracts of the 2nd Clinical Lactoferrin Symposium 2009," pages 21 to 27 (Keiichi Shimazaki), Peptides. 2011 September; 32(9): 1953-63. Epub 2011 Jul. 30, Discovery and development of a synthetic peptide derived from lactoferrin for clinical use, Brouwer C P, Rahman M, Welling M M, Biometals. 2010 June; 23(3):493-505. Epub 2010 Mar. 18, The human lactoferrin-derived peptide hLF1-11 primes monocytes for an enhanced TLR-mediated immune response, van der Does A M, Bogaards S J, Jonk L, Wulferink M, Velders M P, Nibbering P H, J Agric Food Chem. 2010 Jun. 9; 58(11): 6721-7, Antihypertensive properties of lactoferricin B-derived peptides, Ruiz-Gimenez P, Ibanez A, Salom J B, Marcos J F, Lopez-Diez J J, Valles S, Torregrosa G, Alborch E, Manzanares P), which may be designed as needed.

In relation to the fusion protein or the like of the present invention, the term "biological activity" is intended to mean the physiological or pharmacological activity of lactoferrin, unless otherwise specified. In particular, the fusion protein or the like of the present invention has the same iron-chelating (binding) ability as natural lactoferrin (or recombinant lactoferrin having a sequence equivalent to that of natural lactoferrin). More specifically, assuming that the iron-binding ability of natural lactoferrin (or recombinant lactoferrin having a sequence equivalent to that of natural lactoferrin) is set to 100%, as measured in the manner described later in the Example section, the fusion protein or the like of the present invention retains at least 50% or more (e.g., about 50% to about 150% or about 50% to about 120%) of the iron-binding ability. In a preferred embodiment, the fusion protein or the like of the present invention has iron-binding ability which corresponds to about 70% to about 100% or more (e.g., about 70% to about 150% or about 70% to about 120%), more particularly about 90% or more of that of natural lactoferrin (or recombinant lactoferrin having a sequence equivalent to that of natural lactoferrin). It should be noted that when the iron-binding ability is measured in the manner described in the Example section or in a manner equivalent thereto, there may be an error around ±20%.

The fusion protein of the present invention may further comprise an additional amino acid sequence and(or) a sugar chain, etc. The fusion protein of the present invention may have any amino acid sequence whose length is suitable for use as a spacer sequence between the protein or peptide comprising an FcRn-binding region and lactoferrin or a biologically active fragment or peptide of lactoferrin. Such a spacer sequence (s) may be, for example, any amino acid sequence of 0 to 10 residues or 0 to 5 residues. Other additional sequences may be those providing three-dimensional structural advantages, as in the case of a spacer sequence, or may be those imparting some kind of function to the fusion protein, as exemplified by signal peptides or tag sequences used for purification purposes. Fusion proteins having these additional elements are referred to as variants.

The fusion protein or the like of the present invention can be prepared by gene recombination technology. A lactoferrin gene having a desired amino acid sequence and a gene for the protein or peptide comprising an FcRn-binding region may be linked in a standard manner to construct an expression vector comprising other elements required for expression in desired host cells, and this vector may then be introduced into the host cells to express a fusion protein, followed by collecting the expressed fusion protein from the cells or medium.

A nucleic acid molecule encoding the fusion protein or the like of the present invention can be designed and prepared by using known sequences and standard genetic engineering techniques. Genes encoding lactoferrin and the protein comprising an FcRn-binding region can be obtained by being cloned from commonly available various genomic or cDNA libraries with the use of probes based on known nucleic acid or amino acid sequences or by being synthesized by polymerase chain reaction (PCR). It is also possible to make desired modifications to these genes or introduce mutations into these genes.

A host cell-vector system used for replication of the nucleic acid molecule and a host-vector system used for expression of the fusion protein may be selected as appropriate from among many known systems of eukaryotic cells (e.g., mammalian cells, plant cells, yeast, insect cells) and prokaryotic cells (e.g., bacteria).

In addition to a sequence encoding lactoferrin or a biologically active fragment or peptide of lactoferrin and a sequence encoding the protein or peptide comprising an FcRn-binding region (or alternatively, a sequence encoding the protein or peptide comprising an FcRn-binding region and a sequence encoding lactoferrin or a biologically active fragment or peptide of lactoferrin), the vector used to express the fusion protein of the present invention generally comprises, in an operably linked state, a transcription promoter, a secretory signal peptide sequence, a transcription terminator, a polyA signal and other elements, and usually further comprises a selective marker such as a drug resistance gene.

These vectors may be used to transform host cells in accordance with various known techniques.

The fusion protein or the like of the present invention can be produced by genetically modified plants and genetically modified animals prepared for this purpose. For example, a nucleic acid molecule encoding the fusion protein of the present invention may be integrated into the non-human animal (e.g., sheep, goat) genome to thereby allow the fusion protein of the present invention to be secreted into milk. Alternatively, upon integration into plants, it is possible to prepare useful plants which produce the fusion protein or the like of the present invention (see, e.g., JP 2004-528022 A).

The fusion protein or the like of the present invention can be isolated and purified from the medium or the like of host cells transformed with the expression vector of the present invention by using ammonium sulfate precipitation, gel filtration, and various chromatographic techniques such as ion exchange chromatography and affinity chromatography, as appropriate. A particularly preferred purification technique is ion exchange chromatography.

Lactoferrin has a wide range of physiological activities including an antibacterial effect, an iron metabolism regulatory effect, a cell proliferation activation effect, a hematopoietic effect, an anti-inflammatory effect, an antioxidative effect, a phagocytosis enhancement effect, an antiviral effect, a bifidobacteria growth promotion effect, an anticancer effect, a cancer metastasis inhibitory effect, a translocation inhibitory effect, a lipid metabolism improvement effect, an analgesic effect, an anti-stress effect and so on, and these effects allow treatment (including amelioration) and prevention of many diseases or symptoms including lifestyle-related diseases (e.g., hypercholesterolemia, hyperlipidemia), pain control (e.g., cancer pain, neuropathic pain), collagenosis (e.g., dry eye and dry mouth associated with Sjogren's syndrome, rheumatic arthritis), periodontal disease, hepatitis C, etc.

The fusion protein or the like of the present invention fully retains the biological activities of lactoferrin, and hence can be administered as a prophylactic or therapeutic agent for diseases against which lactoferrin is effective, either alone or in combination with other pharmaceutical agents. Moreover, the fusion protein or the like of the present invention can be formulated into pharmaceutical compositions in desired dosage forms by being blended with various carriers, therapeutically inert bases and/or additives known in the pharmaceutical field. For convenience' sake, the term "pharmaceutical preparation" or "pharmaceutical composition" used in relation to the present invention is intended to include not only cases where targets to be administered are humans, but also cases where targets to be administered are animals (i.e., veterinary drugs and the like). Various ingredients, which can be contained in such a pharmaceutical composition, and possible dosage forms are well known to those skilled in the art.

The effective dose of a therapeutic agent or pharmaceutical composition comprising the fusion protein or the like of the present invention will vary depending on the type or severity of disease or symptom to be treated or prevented, the state of a target to be administered, the intended dosage form, the route of administration and so on, and hence may be selected as appropriate based on the known effective dose of lactoferrin. In general, it is possible to select a significantly lower dose (e.g., $\frac{1}{2}$ to $\frac{1}{20}$, calculated as the amount of lactoferrin) in comparison with the known effective dose of lactoferrin. Alternatively, when used at the same dose, the therapeutic agent or pharmaceutical composition can be administered at a reduced frequency.

EXAMPLES

The present invention will be further described in more detail by way of the following examples and test examples, although the present invention is not limited only to the scope illustrated in the Example section.

Example 1: Preparation of a Fusion Protein Formed with Human Lactoferrin (hLF) and a Hinge Region-Containing Human IgG Fc Region, and Evaluation of its Biological Activities 1. Cloning of Human Lactoferrin (hLF) Gene Human lactoferrin (hLF) cDNA was obtained by PCR from a human cDNA library (trade name "Human Leukocyte Marathon-Ready cDNA," Clontech). Using S_LFex_XhoI_ATG (SEQ ID NO: 1; 5'-CTCGAGATGAAACTTGTCTTCCTCGTC (designed to introduce an XhoI site (underlined) upstream of the initiation codon ATG) as a forward primer and using AS_LFex_TAA_XbaI (SEQ ID NO: 2; 5'-TCTAGATTACTTCCTGAGGAATTCAC (designed to introduce an XbaI site (underlined) downstream of the termination codon TAA) as a reverse primer, hLF cDNA was amplified with DNA synthetase "KOD-plus" (trade name, Toyobo Co., Ltd., Japan).

The resulting DNA fragment was subjected to addition of A and cloned with a "TOPO TA cloning vector" (trade name, Invitrogen). Then, this vector was digested with XhoI and XbaI to excise a DNA fragment of hLF cDNA, which was then cloned into vector "pBluescript II" (trade name, Stratagene) which had been digested with XhoI and XbaI. This vector was designated as "pBSIILfAL." The nucleotide sequence of hLF cDNA was confirmed by dideoxy sequencing. In pBSIILfAL, the full-length hLF gene was cloned in a state sandwiched between XhoI and XbaI restriction enzyme sites in the vector. The structure of pBSIILfAL is shown in FIG. 1 (left panel).

The thus prepared vector pBSIILfAL carrying the full-length hLF gene was used to prepare a vector, pBSIILfAL/Bam, in which a BamHI site was introduced between EcoRI and XbaI located at the 3'-terminal side of the hLF gene. Synthetic oligonucleotides Eco_hLF_Bam-S (SEQ ID NO: 3; 5'-AATTCCTCAGGAAGGATCCT-3') and Eco_hLF_Bam-A (SEQ ID NO: 4; 5'-CTAGAGGATCCT-TCCTGAGG-3') were provided and each dissolved in sterilized water at a concentration of 100 μM. Then, the reagents indicated in Table 1 below were mixed to prepare a sample solution.

TABLE 1

| | |
|---|---|
| 100 μM Eco_hLF_Bam-S (μl) | 10 |
| 100 μM Eco_hLF_Bam-A (μl) | 10 |
| 1M Tris HCl (pH 7.5) (μl) | 0.8 |
| 5M NaCl (μl) | 0.8 |
| Sterilized water (μl) | 20.4 |
| Total (μl) | 42 |

This sample solution was heated to 70° C. and then slowly cooled to room temperature to thereby cause annealing and double-stranded DNA formation (annealing oligo). pBSIILfAL (10 ng/μl), which had been completely digested with EcoRI and XbaI, was provided and the reagents indicated in Table 2 below were mixed to cause ligation at 16° C. for 30 minutes.

TABLE 2

| | |
|---|---|
| Annealing oligo (μl) | 2 |
| pBSIILfAL (μl) | 5 |
| Ligation High (TOYOBO) | 7 |
| Total (μl) | 14 |

This ligation solution (5 μl) and competent cells TOP10 (50 μl) were mixed and incubated on ice for 30 minutes. Then, the competent cells were treated by heat shock at 42° C. for 40 seconds and allowed to stand on ice for 2 minutes, followed by addition of SOC medium (100 μl) and incubation at 37° C. for 1 hour. The sample incubated for 1 hour was seeded onto ampicillin-containing LB agar medium and cultured overnight at 37° C. On the following day, the resulting colonies were cultured overnight with shaking in 1.5 ml of LB liquid medium (containing 100 μg/ml ampicillin) under conditions of 37° C. and 200 rpm.

Plasmid DNA extraction was conducted with a "QIAprep Spin Miniprep Kit" (trade name, QIAGEN). Ligation between the annealing oligo and pBSIILfAL was confirmed by decoding the nucleotide sequence near the annealing oligo. The thus prepared vector was designated as pBSIILfAL/Bam (FIG. 1, right panel).

2. Construction of a Hinge Region-Containing hLF/hIgGFc Fusion Protein Expression Vector 2-1 Construction of pTeuIgG/hLF An expression vector was constructed to allow animal cells to express a fusion protein (hLF/hIgGFc) formed with hLF and human IgG Fc (hIgGFc) in a state dimerized at the hinge region via disulfide (s-s) linkages (which may also be referred to as hinge-added fusion protein d(hLF/hIgGFc)).

Figure 2:
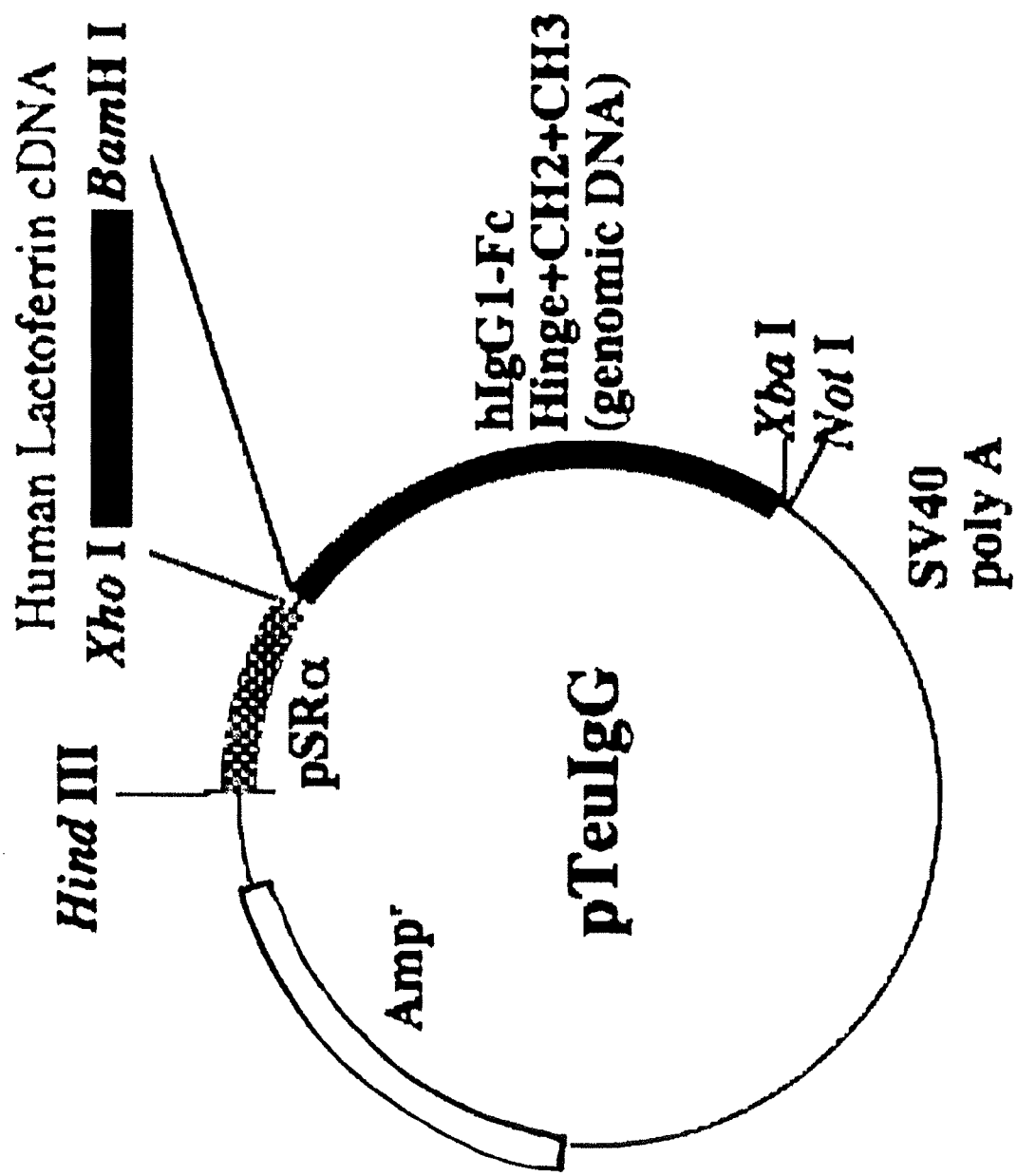
FIG. 2 shows the structure of vector pTeuIgG carrying the genomic sequence of human IgG1 Fc region (hinge, CH2, CH3), along with insertion of hLF cDNA into this vector.

An XhoI-BamHI fragment from pBSIILfAL/Bam was cloned into the XhoI/BamHI site of pTeuIgG (FIG. 2), which is an expression vector carrying the genomic sequence of the hinge, CH2 and CH3 from the human IgG Fc region. This hinge-added fusion protein d(hLF/hIgGFc) expression vector was designated as pTeuIgG/hLF. Preparation of the expression vector was accomplished in the same manner as described above.

It should be noted that pTeuIgG was constructed such that a genomic DNA sequence corresponding to the hinge, CH2 and CH3 regions of human IgG1 was introduced downstream of the strong expression promoter SRα (Sato, A. et al., Biochem. J. 371, 603-608 (2003)).

For construction of a cell line stably expressing the hLF/hIgGFc fusion protein, DHFR-deficient Chinese hamster ovary cells (DG44), a kind of CHO cells, were used. DHFR refers to dihydrofolate reductase and is essential for biosynthesis of nucleic acids. When cells are cultured in the presence of methotrexate (MTX) serving as an antagonist of DHFR, DHFR production is inhibited. In this state, it is known that the cells amplify the DHFR gene for their survival, as a result of which genes located near the DHFR gene are also amplified and protein expression of these genes are therefore amplified. In this way, a target protein can be highly expressed.

Figure 4:
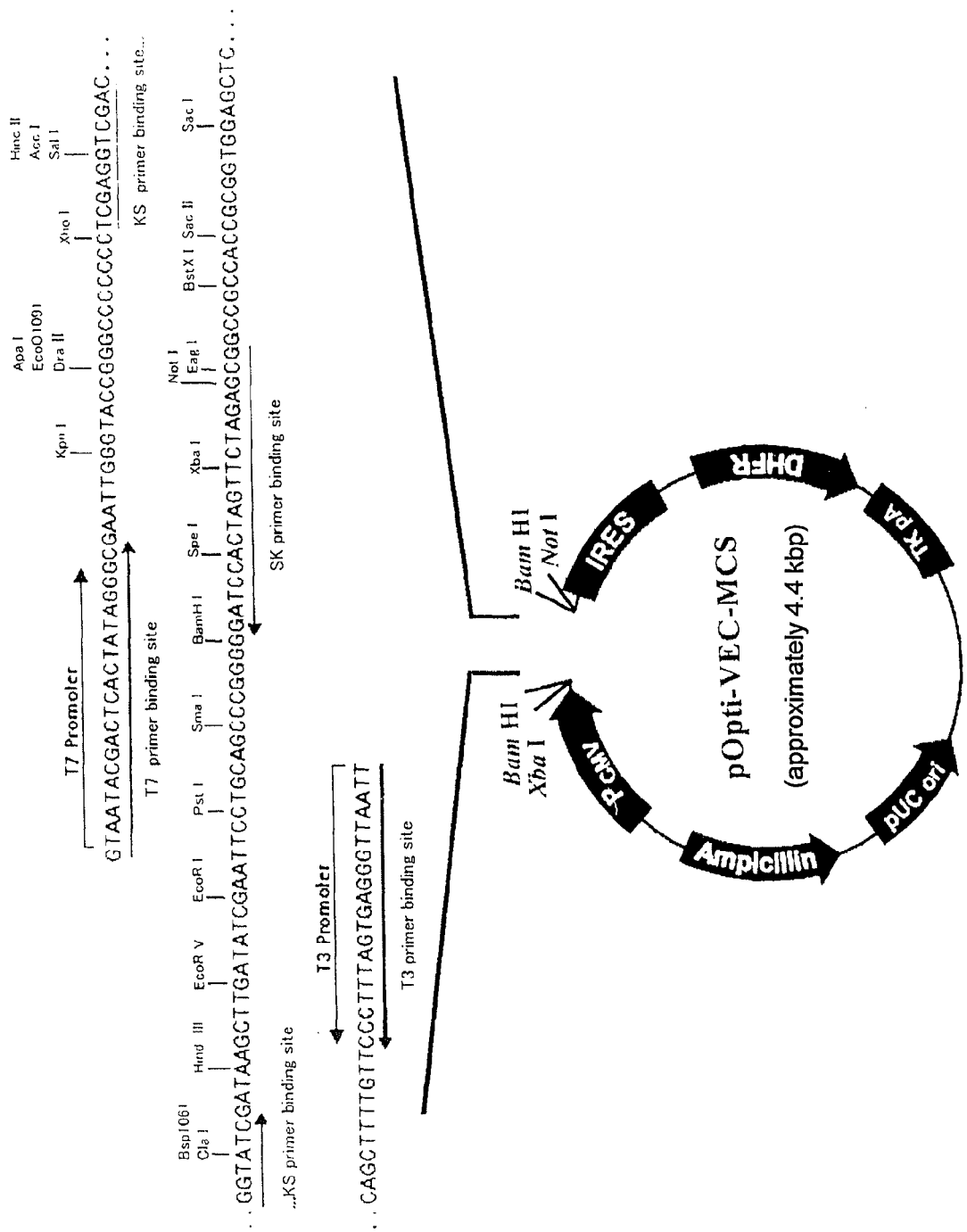
FIG. 4 shows a schematic representation where a region covering from the T7 primer binding site to the T3 primer binding site of vector pBluescript II (Stratagene) is inserted into pOpti-VEC, an expression vector for DG44 cells, to thereby prepare vector pOpti-VEC-MCS.

As an expression vector for DG44 cells, pOptiVEC (trade name, Invitrogen) was used. A region covering from the T7 primer binding site to the T3 primer binding site of vector pBluescript II (trade name, Stratagene) was amplified by PCR and ligated to pOptiVEC by TA cloning to prepare vector pOptiVEC-MCS (FIG. 4).

Figure 5:
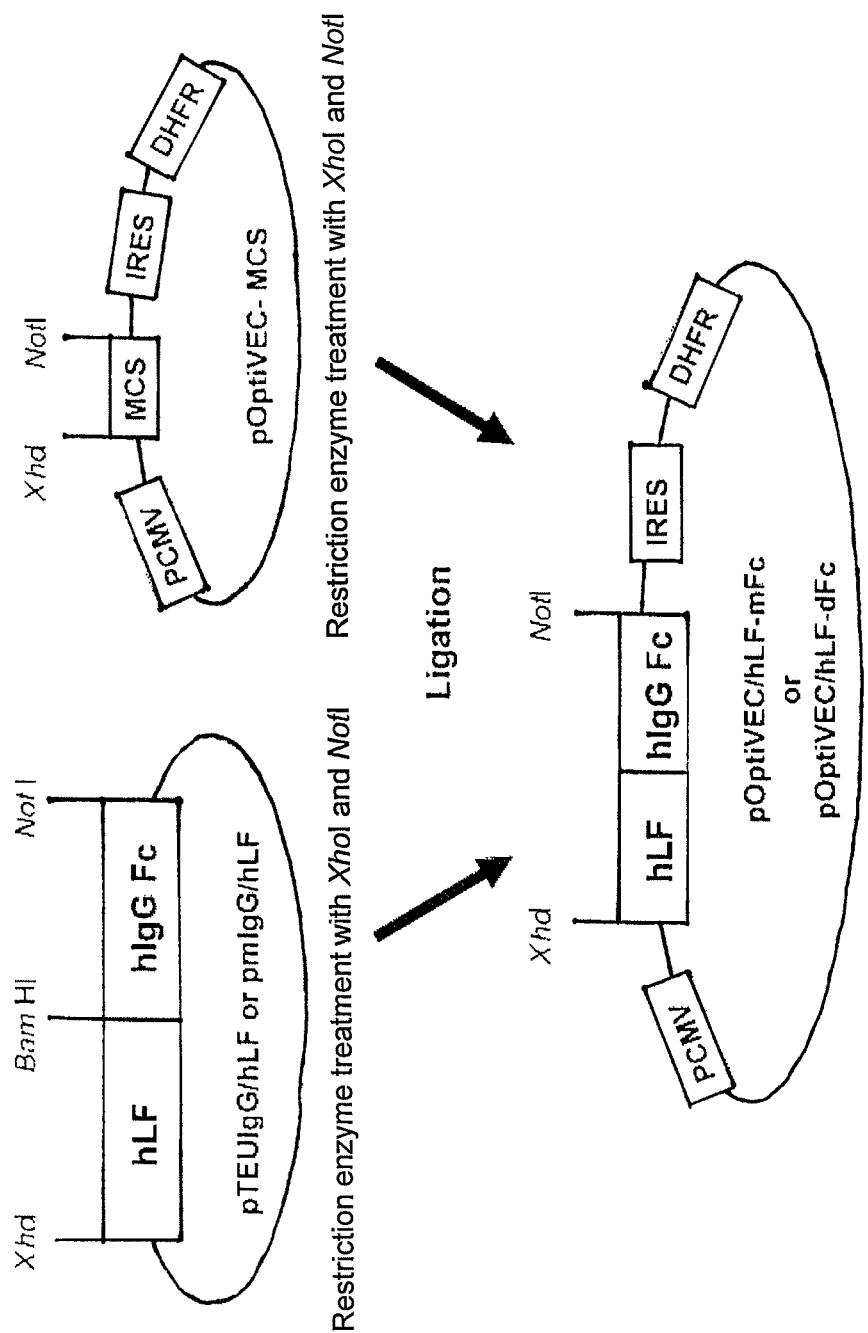
FIG. 5 shows a schematic representation of how to prepare a hinge-added fusion protein d(hLF/hIgGFc) expression vector and a hinge-deficient fusion protein hLF/mhIgGFc expression vector. A region comprising hLF and the genomic sequence of human IgG Fc region (hinge, CH2, CH3) from pTeuIgG/hLF or a region comprising the cDNA sequence of human IgG Fc region (CH2, CH3) from pmIgG/hLF was excised as a XhoI-NotI fragment and cloned into the XhoI/NotI site of pOptiVEC-MCS.

For construction of the hinge-added fusion protein d(hLF/hIgGFc) expression vector, a region including the genomic sequences of hLF and the human IgG Fc region (hinge, CH2, CH3) was excised as an XhoI-NotI fragment from the vector pTeuIgG/hLF and cloned into the XhoI/NotI site of pOptiVEC-MCS. This vector was designated as pOptiVEC/hLF-dFc (FIG. 5). Preparation of the expression vector was accomplished in the same manner as described above.

The amino acid sequence of the human lactoferrin (hLF)/human IgG Fc fusion protein encoded by the hinge-added fusion protein d(hLF/hIgGFc) expression vector pOptiVEC/hLF-dFc is shown in SEQ ID NO: 5 in the Sequence Listing. In SEQ ID NO: 5, amino acids 1 to 711 correspond to an amino acid sequence for hLF, amino acids 712 to 714 correspond to an amino acid sequence for a spacer, amino acids 715 to 729 correspond to an amino acid sequence for the hinge region, amino acids 730 to 839 correspond to an amino acid sequence for the CH2 domain, and amino acids 840 to 946 correspond to an amino acid sequence for the CH3 domain (FIG. 17A: based on the sequences under Genbank registration Nos. AAB60324.1. and AAA02914.1).

3. Expression and Purification of the Hinge-Added hLF/hIgGFc Fusion Protein 3-1. Construction of a Cell Line Stably Expressing the Hinge-Added hLF/hIgGFc Fusion Protein by Using DG44 Cells as a Host The thus prepared pOptiVEC/hLF-dFc was introduced into DG44 cells to establish a cell line stably expressing the hinge-added fusion protein d(hLF/hIgGFc). For efficient introduction of the expression vector into the cells, 20 µg of the vector was linearized by restriction enzyme treatment with PvuI. This sample was supplemented with 1 volume of phenol/chloroform and shaken with a mixer (Vortex) to remove proteins. After centrifugation at 15000 rpm for 5 minutes, the supernatant was transferred to a new tube. The supernatant was supplemented with 1/10 volumes of 3 M sodium acetate and 2.5 volumes of 100% ethanol, followed by centrifugation at 15000 rpm for 20 minutes to precipitate the vector. After removal of the supernatant, the tube was rinsed by addition of 70% ethanol (100 µl). Then, the tube was centrifuged at 15000 rpm for 5 minutes to remove the supernatant, followed by air drying for 10 minutes. To the air-dried tube, sterilized water (15 µl) was added to suspend the expression vector. The PvuI-treated expression vector was designated as pOptiVEC/hLF-dFc/PvuI.

The thus prepared pOptiVEC/hLF-dFc/PvuI was used to transfect DG44 cells. 20 µg of pOptiVEC/hLF-dFc/PvuI was mixed with 15 µl of "Free Style MAX Reagent" (trade name, Invitrogen) and with 1200 µl of "Opti Pro SFM" (trade name, Invitrogen), and then allowed to stand at room temperature for 10 minutes, and assumed it a transfection solution. DG44 cells ($15\times10^6$ cells) were suspended in 30 ml medium ("complete CD DG44 medium," Invitrogen) and the transfection solution prepared in advance was mixed thereinto, followed by culture in a $CO_2$ incubator (37° C., 5% $CO_2$) for 48 hours. Then, the "complete CD DG44 medium" was replaced with "complete CD opti CHO medium" (Invitrogen). This medium is a hypoxanthine- and thymidine-free medium in which DHFR-deficient cells cannot grow. On the other hand, the expression vector treated with restriction enzyme PvuI encodes the DHFR gene, so that DG44 cells will be able to grow when the expression vector is integrated into their chromosome. The cells after 48 hours from the transfection were collected by centrifugation at 400×g for 5 minutes and suspended in 30 ml of "complete CD opti CHO medium" ($3\times10^6$ cells/ml). Then, while repeating medium replacement every 2 days, the cells were cultured in a $CO_2$ incubator (37° C., 5% $CO_2$). Culture was continued until the cell density reached 90% or more of the initial cell density at the beginning of culture.

Then, intracellular genome amplification was conducted with methotrexate (MTX, Wako Pure Chemical Industries, Ltd., Japan). The DG44 cells cultured in "Complete CD opti CHO medium" were counted and $1.2\times10^7$ cells were then centrifuged at 400×g for 5 minutes. These cells were suspended in a mixed medium containing 30 ml of "complete CD opti CHO medium" and 1.5 µl of 1 mM MTX (final concentration: 0.05 µM). Then, the cells were cultured in a $CO_2$ incubator (37° C., 5% $CO_2$) until the cell density reached 90% or more of the initial cell density at the beginning of culture. Subsequently, the MTX concentration was increased to 0.5 µM, 1 µM, 2 µM, 3 µM and 4 µM in a stepwise fashion and culture was repeated.

3-2. Confirmation of Hinge-Added hLF/hIgGFc Fusion Protein Expression

The cells ($1.2\times10^7$ cells) were suspended in "complete CD opti CHO medium" containing MTX at each concentration (0 µM, 0.05 µM, 0.5 µM, 1 µM, 2 µM, 3 µM or 4 µM) and cultured in a $CO_2$ incubator (37° C., 5% $CO_2$) until the cell density reached 90% or more of the initial cell density at the beginning of culture. At this time point, the cells were precipitated by centrifugation at 400×g for 5 minutes to collect their supernatant. 15 µl of the supernatant was mixed with 5 µl ft of non-reducing 4× sample buffer (prepared from 2 ml of 0.5 M Tris-HCl (pH 6.8), 0.8 g of sodium lauryl sulfate (Nacalai Tesque, Inc., Japan) and 4 ml of glycerine (Wako), which were mixed and messed up to 10 ml with pure water), and then treated by heating at 95° C. for 5 minutes and analyzed by 7.5% SDS-PAGE. For band staining, CBB was used.

Figure 6:
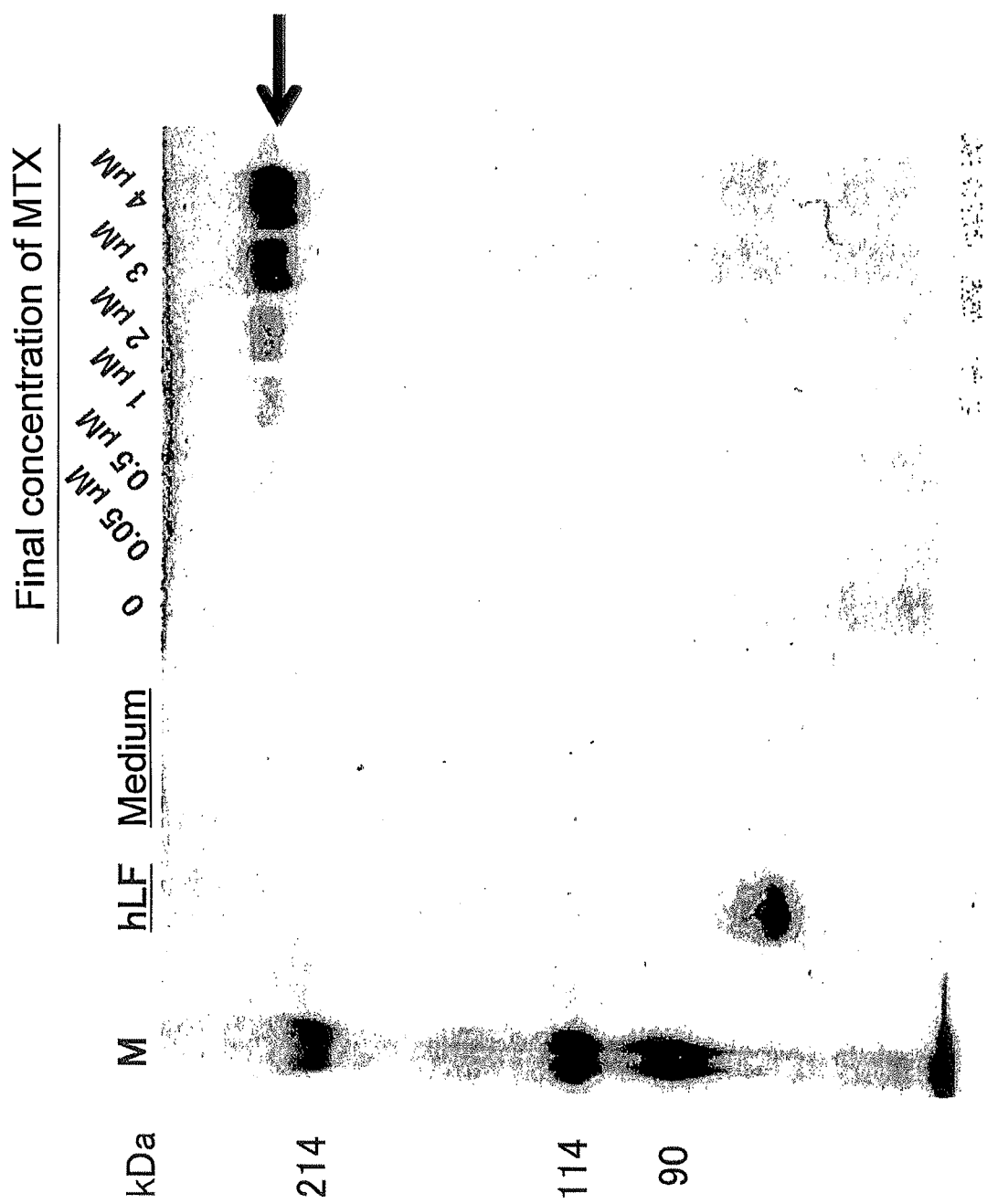
FIG. 6 shows the expression levels obtained when DG44 cells were induced to express the hinge-added fusion protein d(hLF/hIgGFc).

The results obtained are shown in FIG. 6. The molecular weight of the desired protein d(hLF/hIgGFc) is approximately 210 kDa. When the MTX concentration reached 1 µM, a band was observed around approximately 210 kDa indicated with the arrow. With increase in the MTX concentration, the band was stronger, thus confirming that the expression level of the protein was increased.

The cell line establish in the presence of MTX at a concentration of 4 µM was designated as DG44-d(hLF/hIgGFc).

3-3. Large-Scale Expression of the Hinge-Added hLF/hIgGFc Fusion Protein

Large-scale expression was accomplished by static culture using a 175 $cm^2$ T Flask (Greiner, using 50 ml medium) or a Nunc Triple Flask (using 200 ml medium). The cell line stably expressing the hinge-added fusion protein was subcultured in the serum-free medium "Complete CD Opti CHO medium." For protein expression, the medium was replaced with "Hybridoma Serum Free Medium" (trade name, Invitrogen)+4 µM methotrexate (MTX)+60 µg/ml proline (hereinafter referred to as "Hybridoma SFM"), and the cells were seeded at a cell density of $1\times10^6$ cells/ml and cultured at 37° C. in 5% $CO_2$ for 7 days. After 7 days, the cell culture medium was separated into supernatant and cell fractions by centrifugation at 400×g for 5 minutes. The cells were suspended again in 50 ml of Hybridoma SFM and cultured at 37° C. in 5% $CO_2$ for an additional one week to cause protein expression. The supernatant was centrifuged again at 8000 rpm for 5 minutes, and the resulting supernatant was supplemented with sodium azide at a final concentration of 0.02% and stored at 4° C.

3-4. Purification of the Hinge-Added hLF/hIgGFc Fusion Protein

For purification, the culture supernatant (containing sodium azide at a final concentration of 0.02%) obtained by large-scale expression was used directly. 400 µl of "Macro-CaP SP" (trade name, GE Healthcare) serving as a cation exchange carrier was filled into "Poly-Prep Chromatography Columns" (trade name, BioRad Laboratories) and equilibrated with 5 column volumes (CV) of 10 mM sodium phosphate buffer (pH 7.6). The 10 mM sodium phosphate buffer (pH 7.6) used for equilibration was discarded, and 4 ml of the culture supernatant obtained by large-scale expression was then added and reacted in a seesaw shaker for 30 minutes. After the reaction, the solution was collected as a pass-through fraction. The "Poly-Prep Chromatography Columns" were connected to a "UV DETECTOR" (Tokyo Rikakikai Co., Ltd., Japan, measured for absorbance at 280 nm) and a microtube pump (Tokyo Rikakikai Co., Ltd., Japan). The flow rate of the pump was set to 1 ml/min, and 10 mM sodium phosphate buffer (pH 7.6) was passed to wash the carrier. From a time point where the absorbance at 280 nm in the "UV DETECTOR" was started to increase, the eluate was collected (Wash fraction). This eluate collection was continued until the absorbance at 280 nm was 0. Then, the solution was replaced with 0.2 M NaCl+10 mM sodium phosphate buffer (pH 7.6), and the same operations were repeated (0.2 M NaCl-eluted fraction). This series of operations was repeated while increasing the NaCl concentration in increments of 0.1 M up to 1.0 M NaCl. The collected eluates were each stored at 4° C.

15 μl of each eluted fraction was mixed with 5 μl of non-reducing 4× sample buffer, treated by heating at 95° C. for 5 minutes and analyzed by 7.5% SDS-PAGE. For band staining, CBB was used.

Figure 8:
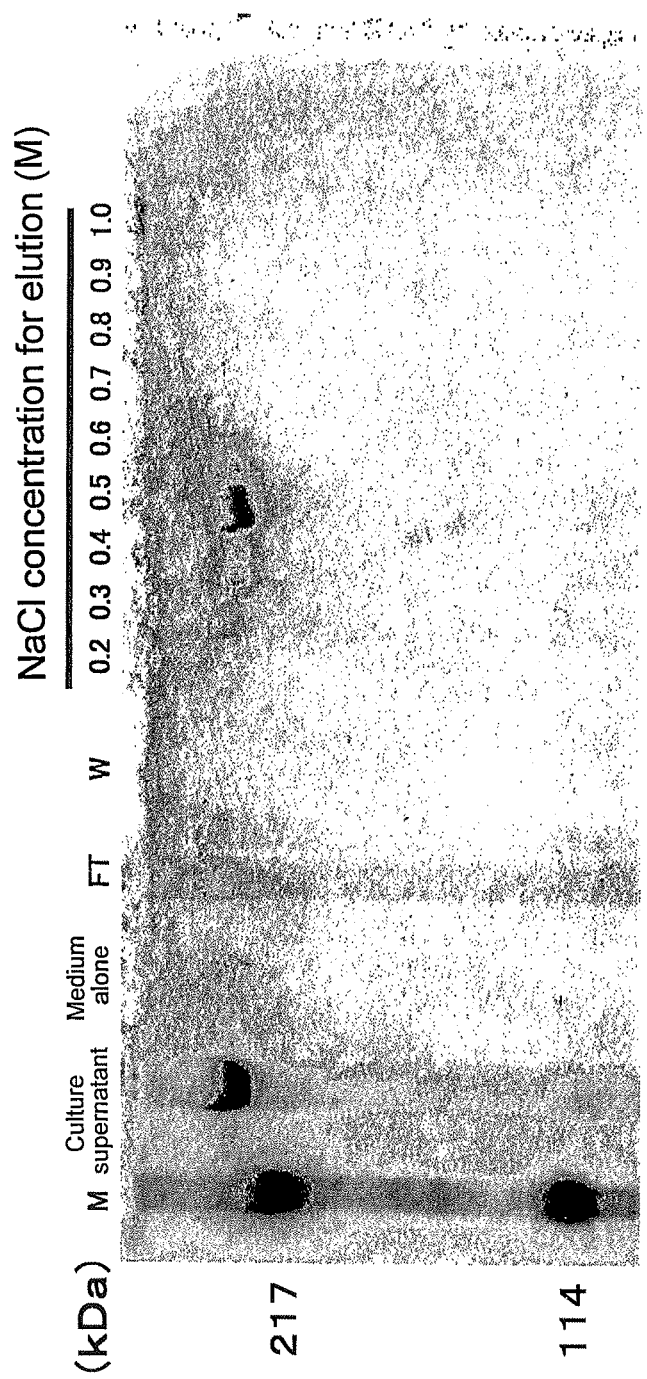
FIG. 8 shows purification of the hinge-added fusion protein d(hLF/hIgGFc).

The results obtained are shown in FIG. 8. The desired protein hinge-added d(hLF/hIgGFc) was found to be eluted from the 0.4 M NaCl fraction. This result indicated that the hinge-added fusion protein d(hLF/hIgGFc) bound to the "MacroCaP SP" would be able to be efficiently collected by being washed with 0.3 M NaCl and eluted with 1.0 M NaCl.

3-5. Concentration of the Hinge-Added hLF/hIgGFc Fusion Protein Through Ammonium Sulfate Precipitation To give 20%, 30%, 40%, 50%, 60%, 70%, 80% and 90% saturation of ammonium sulfate, ammonium sulfate was weighed with a microelectronic balance in amounts per ml of 0.113 g, 0.176 g, 0.242 g, 0.314 g, 0.390 g, 0.472 g, 0.561 g and 0.657 g, respectively, and introduced into 2.0 ml tubes. To the respective tubes, a solution of the hinge-added d(hLF/hIgGFc) protein purified with a cation exchange carrier and suspended in PBS was added in 1 ml volumes and mixed by inversion until ammonium sulfate was dissolved, and the tubes were then allowed to stand overnight at 4° C. Then, the tubes were centrifuged under conditions of 15000 rpm for 30 minutes to precipitate the protein. The supernatants were collected, and the precipitates were each dissolved in 100 μl of PBS. Each precipitate dissolved in PBS and each collected supernatant were analyzed by 7.5% SDS-PAGE and CBB staining.

Figure 10:
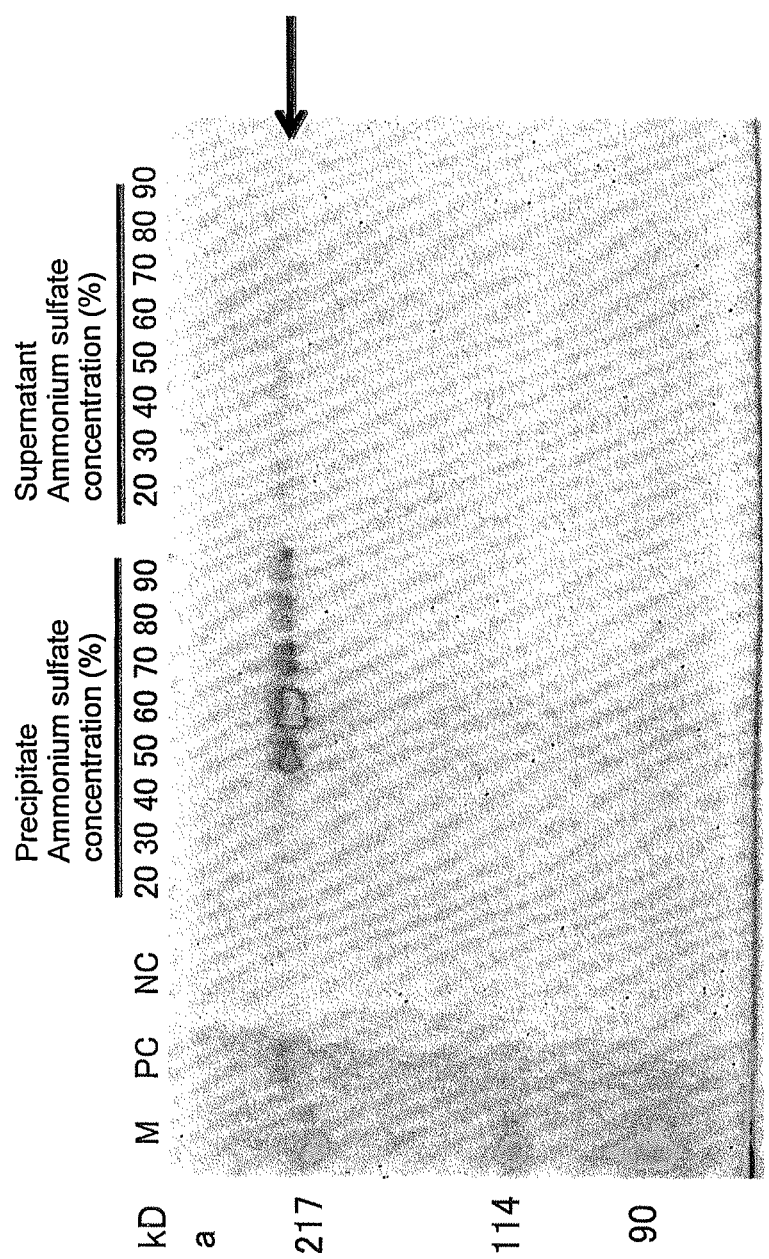
FIG. 10 shows concentration of the hinge-added fusion protein d(hLF/hIgGFc) through ammonium sulfate precipitation.

The results obtained are shown in FIG. 10. Precipitation was observed at 50% to 90% saturation of ammonium sulfate. Further, the fractions showing precipitation at 50% to 90% saturation of ammonium sulfate were measured for their protein concentration in solution by the Bradford assay (protein assay, BioRad Laboratories) using BSA of known concentration as a standard to calculate the recovery rate in ammonium sulfate precipitation (n=5). In the case of the hIgGFc fusion protein, the concentration as hLF was calculated using its molecular weight. More specifically, in the case of the hinge-added fusion protein d(hLF/hIgGFc), calculation was conducted assuming that the molecular weight of hLF was 80 kDa (×2) and the molecular weight of the Fc region was 50 kDa. In the case of the hinge-deficient fusion protein hLF/mhIgGFc, calculation was conducted assuming that the molecular weight of hLF was 80 kDa and the molecular weight of the Fc region was 25 kDa. Each ammonium sulfate concentration and the recovery rate (%) obtained thereat are shown in Table 3 below.

TABLE 3

| Saturated concentration of ammonium sulfate | Recovery rate (%) |
|---|---|
| 50% | 31 (±14.4) |
| 60% | 75 (±10.5) |
| 70% | 79 (±3.7) |
| 80% | 72 (±3.7) |
| 90% | 69 (±8.1) |
| | n = 5 (±S.E.) |

The recovery rate was highest at 70% ammonium sulfate. After ammonium sulfate precipitation, the precipitate was suspended in PBS and dialyzed against PBS to remove ammonium sulfate.

4. Measurement of Biological Activities 4-1. Measurement of the Iron-Binding Ability of the Hinge-Added hLF/hIgGFc Fusion Protein Lactoferrin is a nonheme iron-binding glycoprotein having a molecular weight of 80,000, which is composed of two regions called N-lobe and C-lobe, and has the ability to form reversible chelate bonds with two iron ions (Fe) per molecule of protein in the presence of carbonate ions ($CO_3^{2-}$) (Anderson, et al., Nature, 344, 784-78 (1990)). The iron-binding ability of lactoferrin was measured as follows. Iron ions ($Fe^{3+}$) are released from holo-form lactoferrin to prepare apo-form lactoferrin. Then, iron ions ($Fe^{3+}$) were added in the presence of carbonate ions ($CO_3^{2-}$) to prepare iron-rebound lactoferrin. The thus prepared apo-form lactoferrin and iron-rebound lactoferrin were measured for their iron content and protein concentration to determine the amount of iron bound thereto. More specifically, apo-form lactoferrin was prepared as follows: Aspergillus-derived recombinant human LF or the hinge-added fusion protein d(hLF/hIgGFc) was dialyzed against 0.1 M citrate buffer (pH 2.1) for 24 hours and further dialyzed against distilled water for 24 hours. Iron-rebound lactoferrin was prepared as follows: apo-form lactoferrin was dialyzed against phosphate buffer (pH 7.5) containing 0.001% ammonium iron citrate, 50 mM sodium carbonate and 50 mM sodium chloride for 24 hours and then dialyzed sequentially against distilled water and phosphate buffer (pH 7.5) containing 50 mM sodium chloride for 24 hours to remove excessive iron ions. For colorimetric measurement of iron ions bound to the protein, a serum iron measurement kit "Fe C-Test Wako" (trade name, Wako Pure Chemical Industries, Ltd., Japan) was used. The iron-binding ability was calculated as the amount of iron bound per mg of hLF protein quantified by the Bradford assay (in the case of the human IgG Fc fusion protein, per mg calculated as hLF using its molecular weight). The results of the experiment in duplicate are shown in Table 4 below.

TABLE 4

| Sample name | Amount of iron bound per mg of LF (ng) | | | Relative activity (%) |
| --- | --- | --- | --- | --- |
| | Apo form | Holo form | Iron-binding ability (holo form – apo form) | |
| (First round) Results measured for iron-binding ability | | | | |
| Recombinant hLF | 154.8 | 1321.0 | 1166.1 | 100 |
| Hinge-added fusion protein d(hLF/hIgGFc) | 304.8 | 1362.2 | 1057.4 | 90.7 |
| BSA | 54.6 | 167.8 | — | — |
| (Second round) | | | | |
| Recombinant hLF | 220.9 | 1655.5 | 1434.6 | 100 |
| Hinge-added fusion protein d(hLF/hIgGFc) | 207.1 | 1705.8 | 1498.7 | 104.5 |

Assuming that the iron-binding activity of the *Aspergillus*-derived recombinant hLF was set to 100%, the hinge-added fusion protein d(hLF/hIgGFc) showed nearly 100% activity.

4-2. CD Spectral Study on the Heat Stability of the Hinge-Added hLF/hIgGFc Fusion Protein

*Aspergillus*-derived recombinant hLF and the hinge-added fusion protein d(hLF/hIgGFc) were analyzed for their heat stability by circular dichroism (CD) spectrometry. The circular dichroism (CD) spectrometry is a technique to measure a difference in absorbance between right-handed circularly polarized light and left-handed circularly polarized light when a substance is irradiated at a certain wavelength. This technique can be used to predict the presence or absence, type and content of protein secondary structure.

First, suspensions of *Aspergillus*-derived recombinant hLF and the fusion protein d(hLF/hIgGFc) were prepared at 0.1 mg/ml in PBS(-) and measured for their CD spectra at a wavelength of 200 nm to 250 nm at room temperature (about 20° C.) (using J-720, JASCO Corporation, Japan).

Figure 12A:
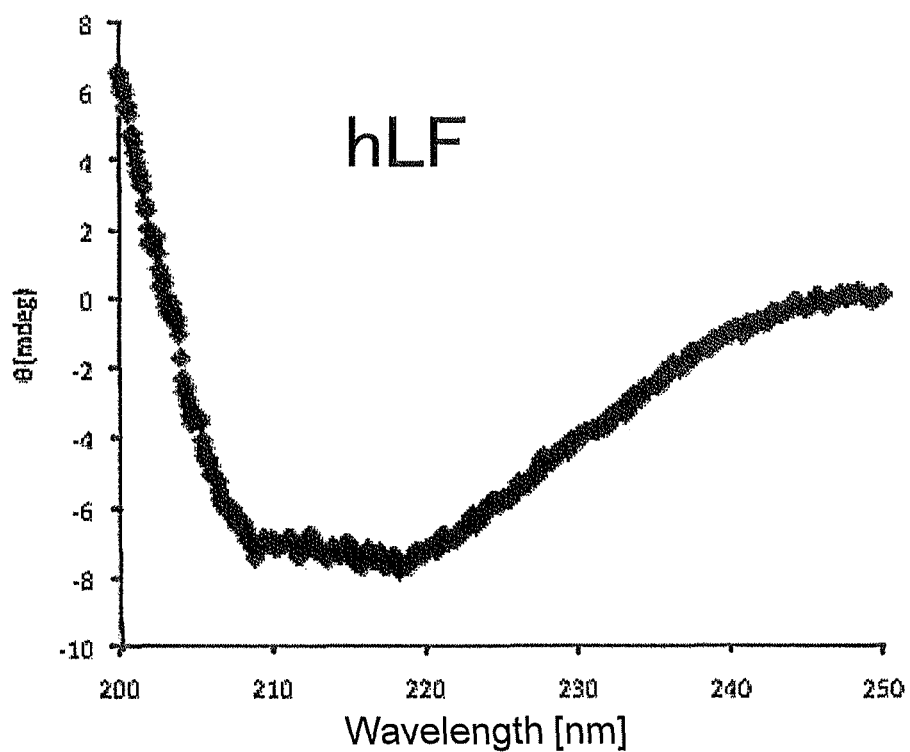
FIG. 12-A shows the secondary structure homology of hLF and the hinge-deficient and hinge-added hLF/hIgGFc fusion proteins. Panel A shows the CD spectrum obtained for hLF.
Figure 12B:
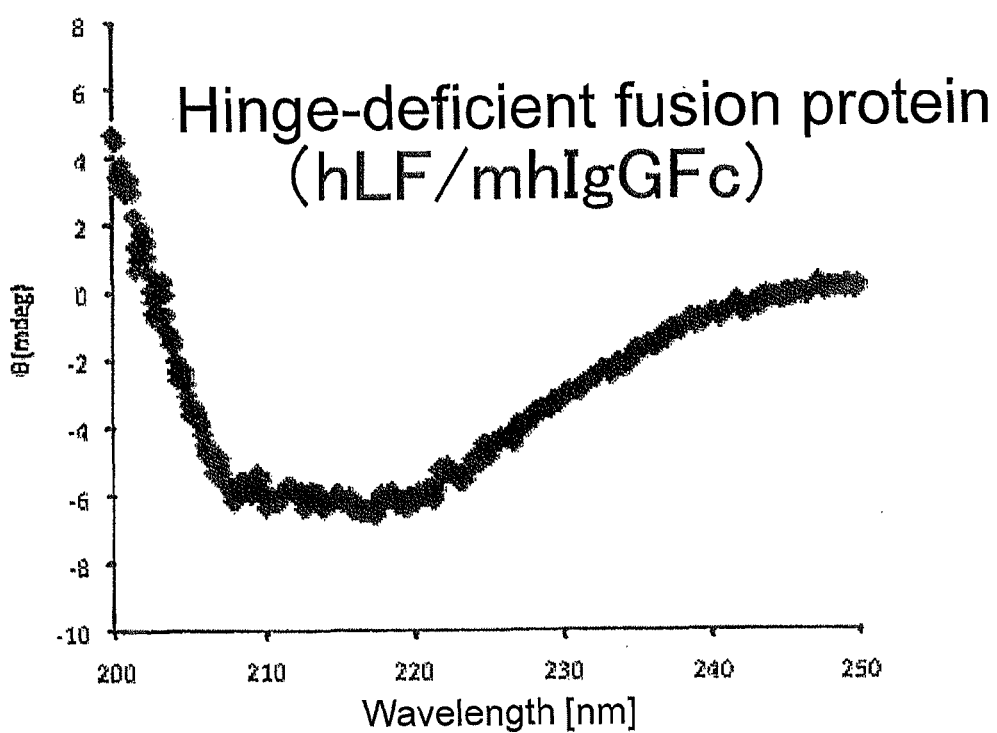
Figure 12C:
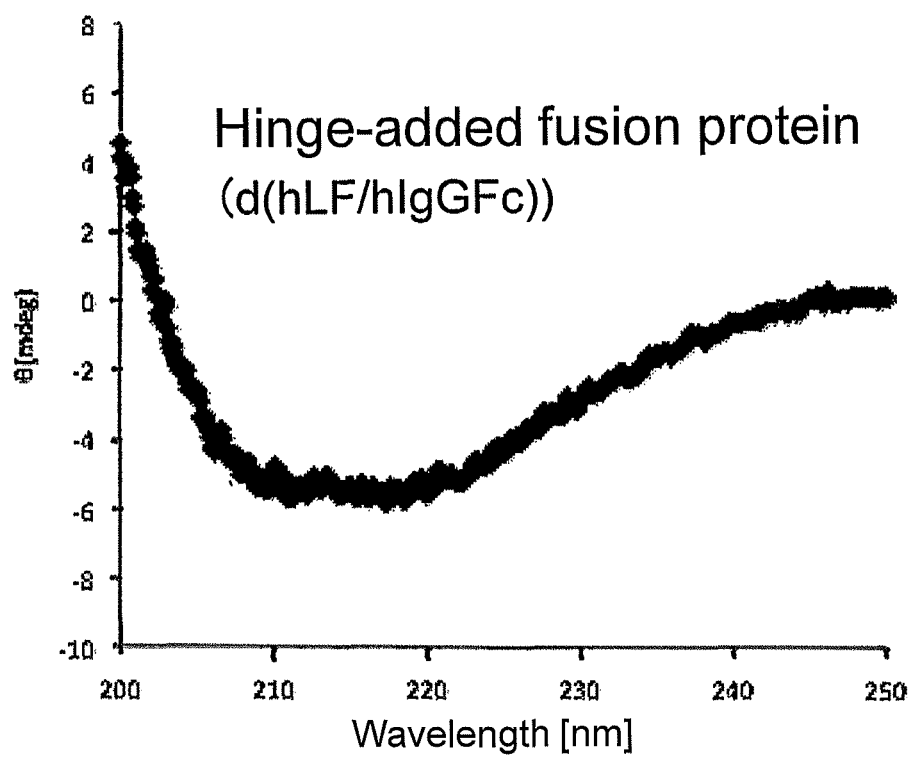

The results obtained are shown in FIG. 12. There was no significant difference in secondary structure between the recombinant hLF (panel A) and the hinge-added fusion protein d(hLF/hIgGFc) (panel C).

Next, each protein was studied for its heat stability. When a CD spectrum is measured while varying the temperature of a protein solution from low temperature to high temperature, [θ] is increased to reach a plateau at a certain temperature. This phenomenon is due to heat-induced denaturation of the protein and the subsequent change in the secondary structure of the protein. For monitoring of heat stability, the wavelength commonly used for measurement is around 225 nm. Suspensions of *Aspergillus*-derived recombinant hLF and the hinge-added fusion protein d(hLF/hIgGFc) were prepared at 0.1 mg/ml in PBS(-) and measured for their CD spectra at a wavelength of 225 nm while increasing the temperature from 30° C. to 90° C. in increments of 1° C. (using J-720, JASCO Corporation, Japan).

Figure 13A:
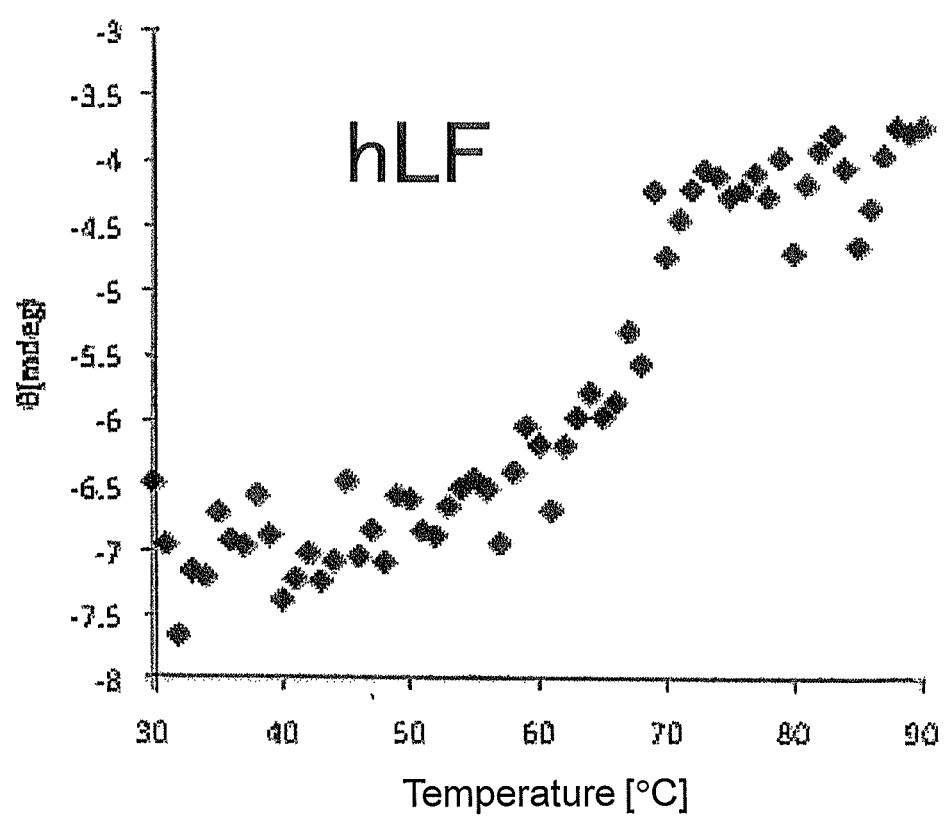
FIG. 13-A shows the heat stability of hLF and the hinge-deficient and hinge-added hLF/hIgGFc fusion proteins. Panel A shows the CD spectrum obtained for hLF.
Figure 13B:
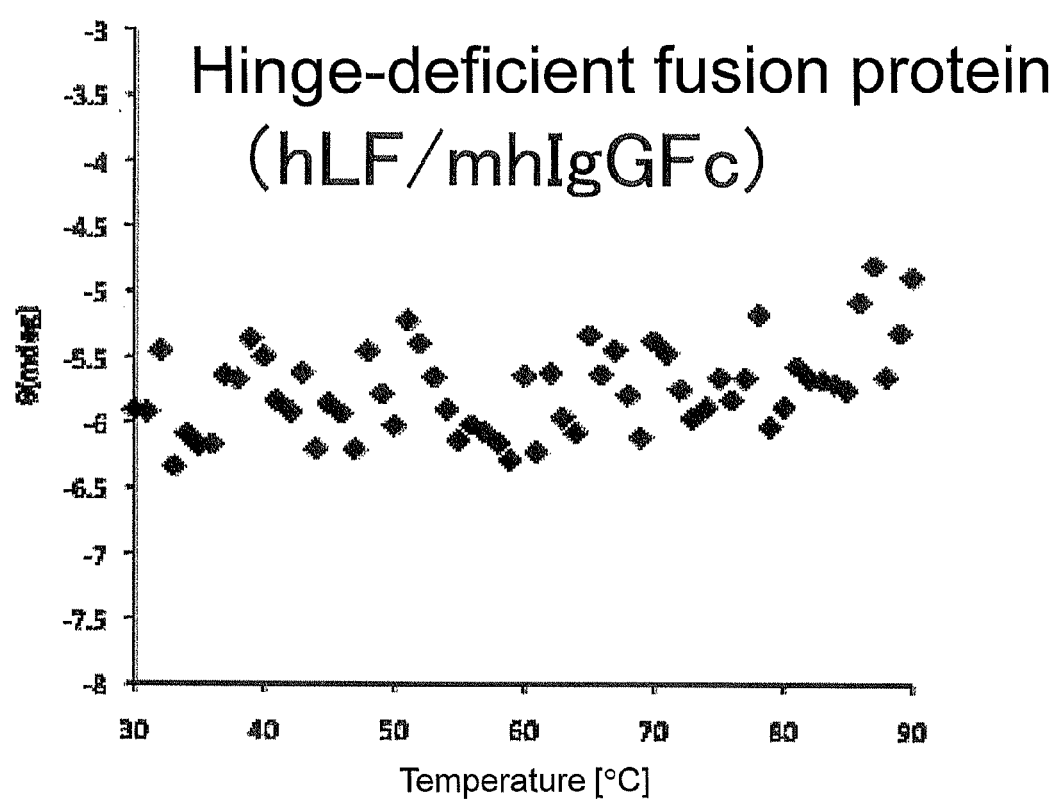
Figure 13C:
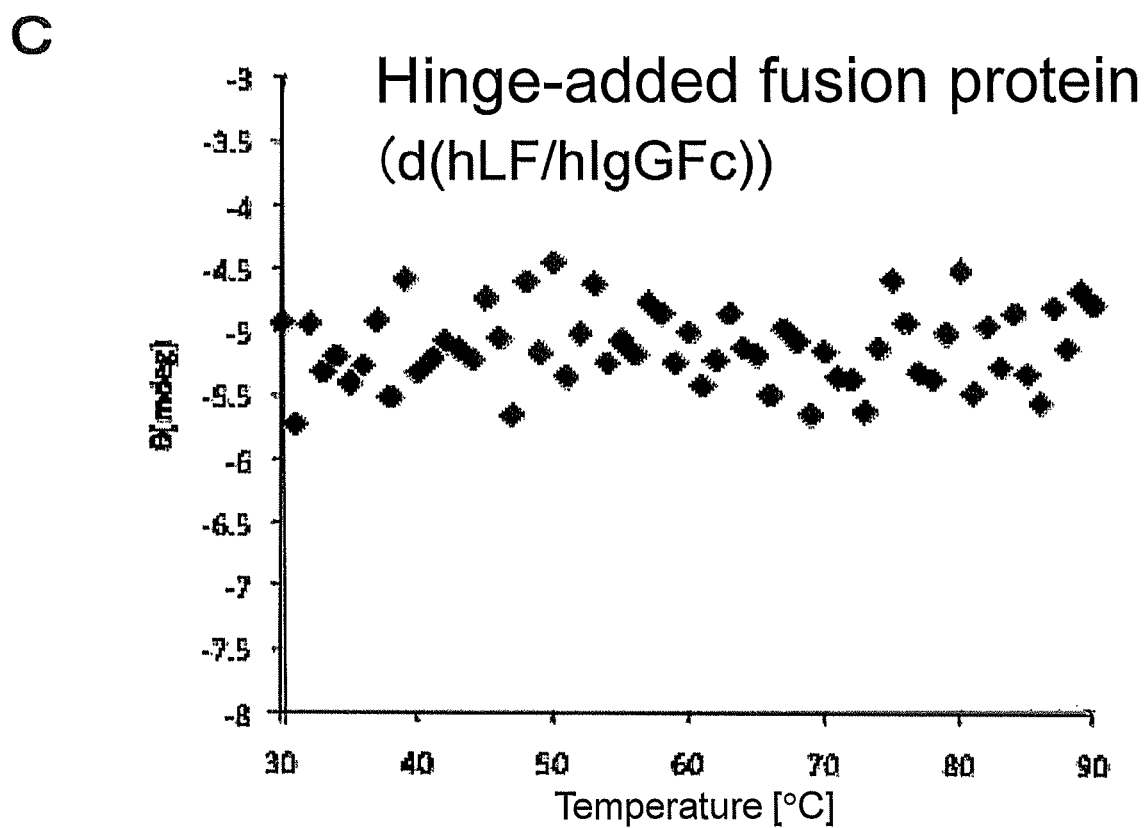

The results obtained are shown in FIG. 13. The *Aspergillus*-derived recombinant hLF (panel A) showed a significant change in its CD spectral values at a temperature around 67° C. In contrast, the hinge-added fusion protein d(hLF/hIgGFc) (panel C) showed no significant change in its CD spectrum at 225 nm even when heated from 30° C. to 90° C.

In view of the foregoing results, when compared to the *Aspergillus*-derived recombinant hLF, the hinge-added fusion protein d(hLF/hIgGFc) was found to have improved stability against heat. The structurally stable hinge-added fusion protein d(hLF/hIgGFc) would also be expected to have improved blood stability in vivo.

4-3. Study on the Stability of the Hinge-Added hLF/hIgGFc Fusion Protein

The hinge-added hLF/hIgGFc fusion protein purified with the cation exchange carrier "MacroCap SP" shown in 3-4 was dialyzed against PBS and further diluted with PBS to prepare a sample of 336 μg/mL concentration. This sample was added in a volume of 100 μL to a 1.5 mL tube and reacted by being allowed to stand at 37° C. for 3 weeks. At 0, 1, 2 and 3 weeks after the reaction, 3 μL of the sample was taken and mixed with 1 μl of non-reducing 4× sample buffer, and then treated by heating at 95° C. for 5 minutes, followed by 7.5% SDS-PAGE for analysis.

Figure 14:
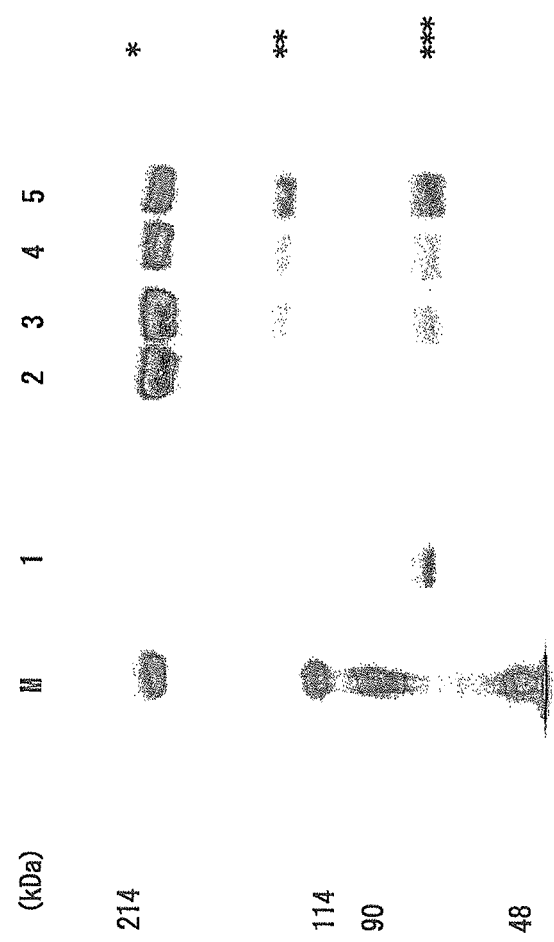
FIG. 14 shows cleavage of the hinge-added hLF/hIgGFc fusion protein.

The results of CBB staining are shown in FIG. 14. In FIG. 14, M represents a marker, Lane 1 represents hLF (1 μg/lane), and Lanes 2 to 5 represent the samples after 0, 1, 2 and 3 weeks, respectively. The fusion protein was stable for a few weeks even at 37° C. However, with the passage of time, the band of the hinge-added hLF/hIgGFc fusion protein indicated with * was found to be weaker, and the bands indicated with  and *, which appear to be cleavage products were found to be stronger. This would be because the fusion protein was cleaved by the action of proteases mixed into during the purification process. It should be noted that such cleavage was not observed for the hinge-deficient fusion protein (described later).

4-4. Analysis of Cleavage Sites in the Hinge-Added hLF/hIgGFc Fusion Protein

Figure 15A:
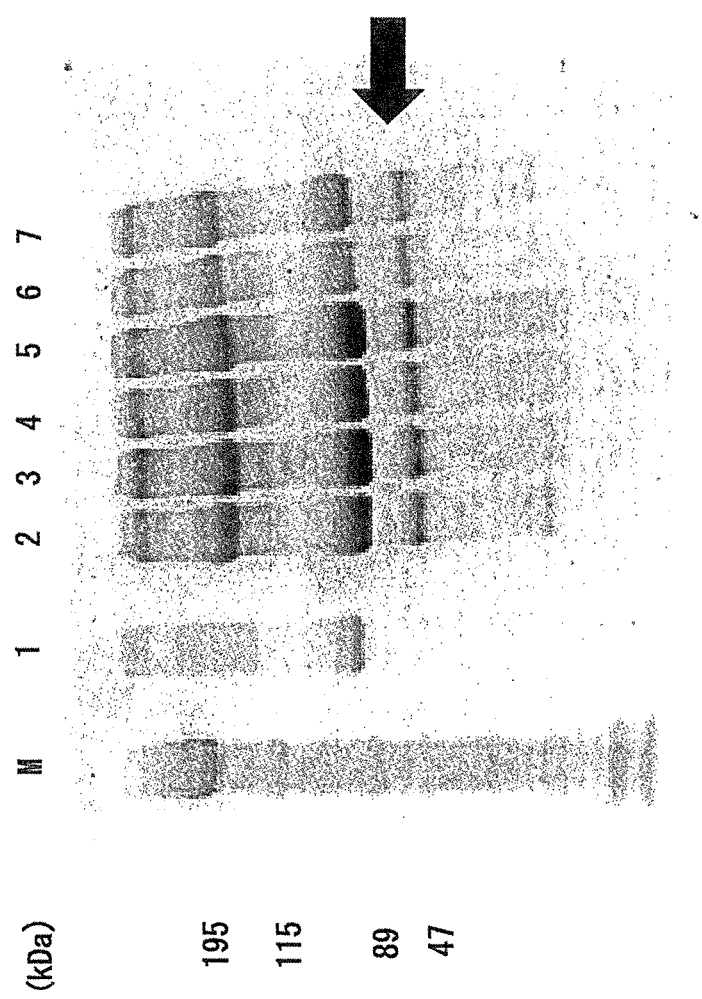
FIG. 15-A shows cleavage products obtained at 37° C. after 3 weeks from the hinge-added hLF/hIgGFc fusion protein.
Figure 15B:
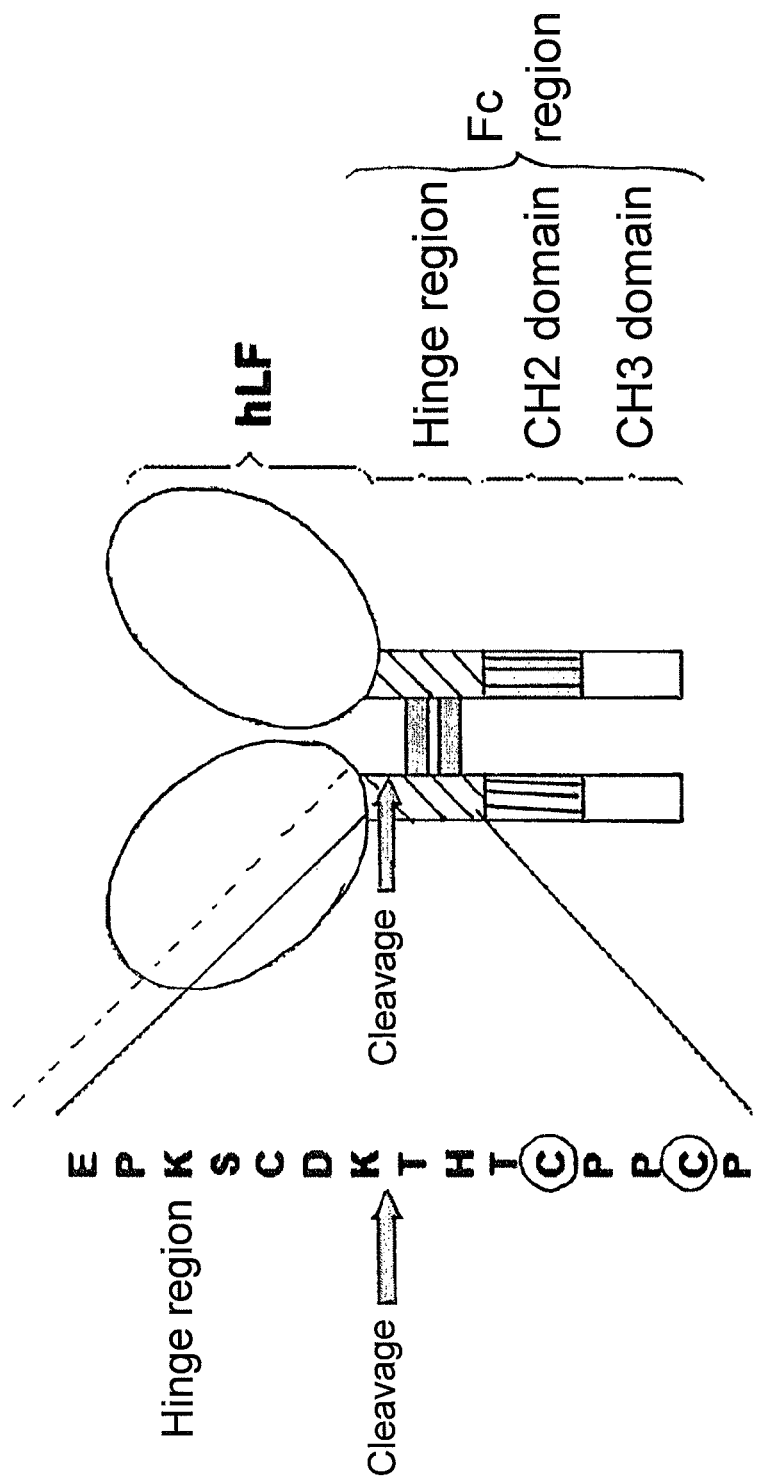

To identify cleavage sites in the hinge-added hLF/hIgGFc fusion protein, the cleavage bands were analyzed for their N-terminal amino acid sequences. In the manner as described above, the hinge-added hLF/hIgGFc fusion protein (12 was reacted by being allowed to stand at 37° C. for 3 weeks, and the cleaved sample was then electrophoresed by 10% SDS-PAGE. After electrophoresis, the protein was transferred onto a PVDF membrane (Millipore Corporation) in a standard manner. The CBB-stained PVDF membrane is shown in FIG. 15-A. In FIG. 15-A, M represents a marker, Lane 1 represents hLF (4 μg), and Lanes 2 to 6 represent the samples after cleavage (2 μg/lane each). From this PVDF membrane, a band of approximately 50 kDa (arrow) was excised and decolorized. The N-terminal amino acid sequence of this band was analyzed with procise 491HT (trade name, ABI). The resulting amino acid sequence was found to be T-H-T-X-P (the fourth amino acid was undecodable). This sequence was further analyzed and found to correspond to amino acids 722 to 726 (within the hinge region) of SEQ ID NO: 5 in the Sequence Listing (FIG. 15-B).

Example 2: Preparation of a Fusion Protein ("Hinge-Deficient") Formed with Human Lactoferrin and a Hinge Region-Free Human IgG Fc Region, and Evaluation of its Biological Activities and Blood Stability 1. Construction of a Hinge-Deficient hLF/hIgGFc Fusion Protein Expression Vector The vector pBSIILfAL/Bam prepared above (FIG. 1) was used to construct an expression vector for allowing animal cells to express a fusion protein (hinge-deficient hLF/mhIgGFc) formed with hLF and hinge region-free hIgGFc.

Figure 3:
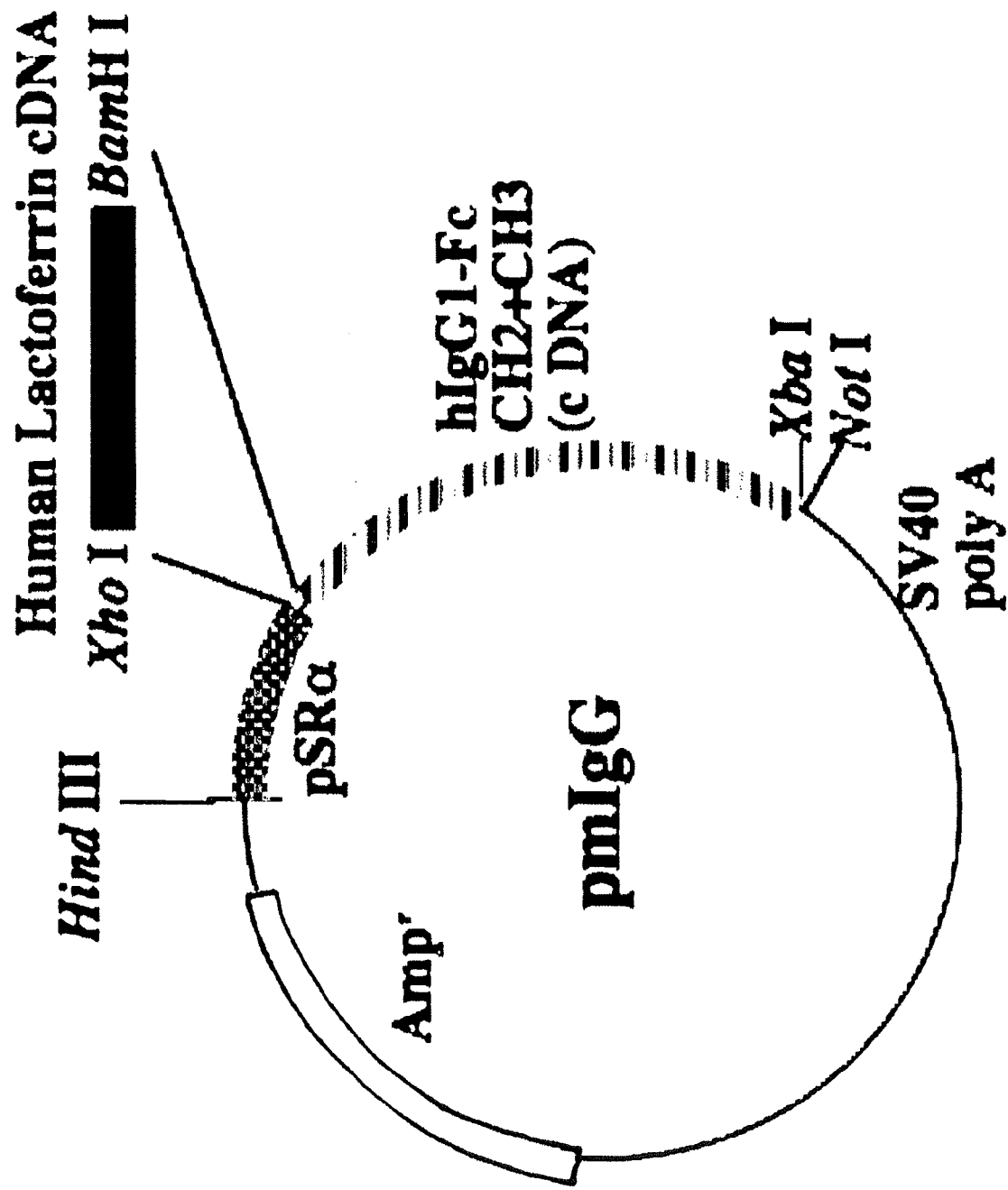
FIG. 3 shows the structure of vector pmIgG carrying the cDNA sequence of human IgG1 Fc region (CH2, CH3), along with insertion of hLF cDNA into this vector.

To prepare such a hinge-deficient fusion protein hLF/mhIgGFc expression vector, an XhoI-BamHI fragment from pBSIILfAL/Bam was cloned into the XhoI/BamHI site of pmIgG (FIG. 3), which is an expression vector carrying the cDNA sequence of CH2 and CH3 from the human IgG Fc region. This vector was designated as pmIgG/hLF. Preparation of each expression vector was accomplished in the same manner as described above.

It should be noted that pmIgG was constructed such that the genomic DNA sequence corresponding to the hinge, CH2 and CH3 regions of human IgG1 located between BamHI and XbaI of the above hinge-added fusion protein expression vector pTeuIgG was replaced with a cDNA sequence corresponding to the CH2 and CH3 regions of human IgG1.

For construction of the hinge-deficient fusion protein hLF/mhIgGFc expression vector, a region including the cDNA sequences of hLF and the human IgG Fc region (CH2, CH3) was excised from pmIgG/hLF as an XhoI-NotI fragment and cloned into the XhoI/NotI site of pOptiVEC-MCS prepared above (FIG. 4). This vector was designated as pOptiVEC/hLF-mFc (FIG. 5). Preparation of the expression vector was accomplished in the same manner as described above. The amino acid sequence of the hLF/hIgGFc fusion protein encoded by the hinge-deficient fusion protein hLF/mhIgGFc expression vector pOptiVEC/hLF-mFc is shown in SEQ ID NO: 6 in the Sequence Listing. In SEQ ID NO: 6, amino acids 1 to 711 correspond to an amino acid sequence for hLF, amino acids 712 to 713 correspond to an amino acid sequence for a spacer, amino acids 714 to 823 correspond to an amino acid sequence for the CH2 domain, and amino acids 824 to 930 correspond to an amino acid sequence for the CH3 domain (FIG. 17B: based on the sequences under Genbank registration Nos. AAB60324.1 and AAA02914.1).

2. Expression and Purification of the Hinge-Deficient hLF/hIgGFc Fusion Protein 2-1. Construction of a Cell Line Stably Expressing the Hinge-Deficient hLF/hIgGFc Fusion Protein by Using DG44 Cells as a Host In the same manner as in the case of the hinge-added fusion protein, the thus prepared pOptiVEC/hLF-mFc was introduced into DG44 cells to establish a cell line stably expressing the hLF/hIgGFc fusion protein. The PvuI-treated expression vector was designated as pOptiVEC/hLF-mFc/PvuI.

In the same manner as in the case of the hinge-added fusion protein, the thus prepared pOptiVEC/hLF-mFc/PvuI was used to transfect DG44 cells, and culture was repeated while increasing the MTX concentration in a stepwise fashion.

2-2. Confirmation of Hinge-Deficient hLF/hIgGFc Fusion Protein Expression

In the same manner as in the case of the hinge-added fusion protein, protein expression was analyzed by 7.5% SDS-PAGE and CBB staining.

Figure 7:
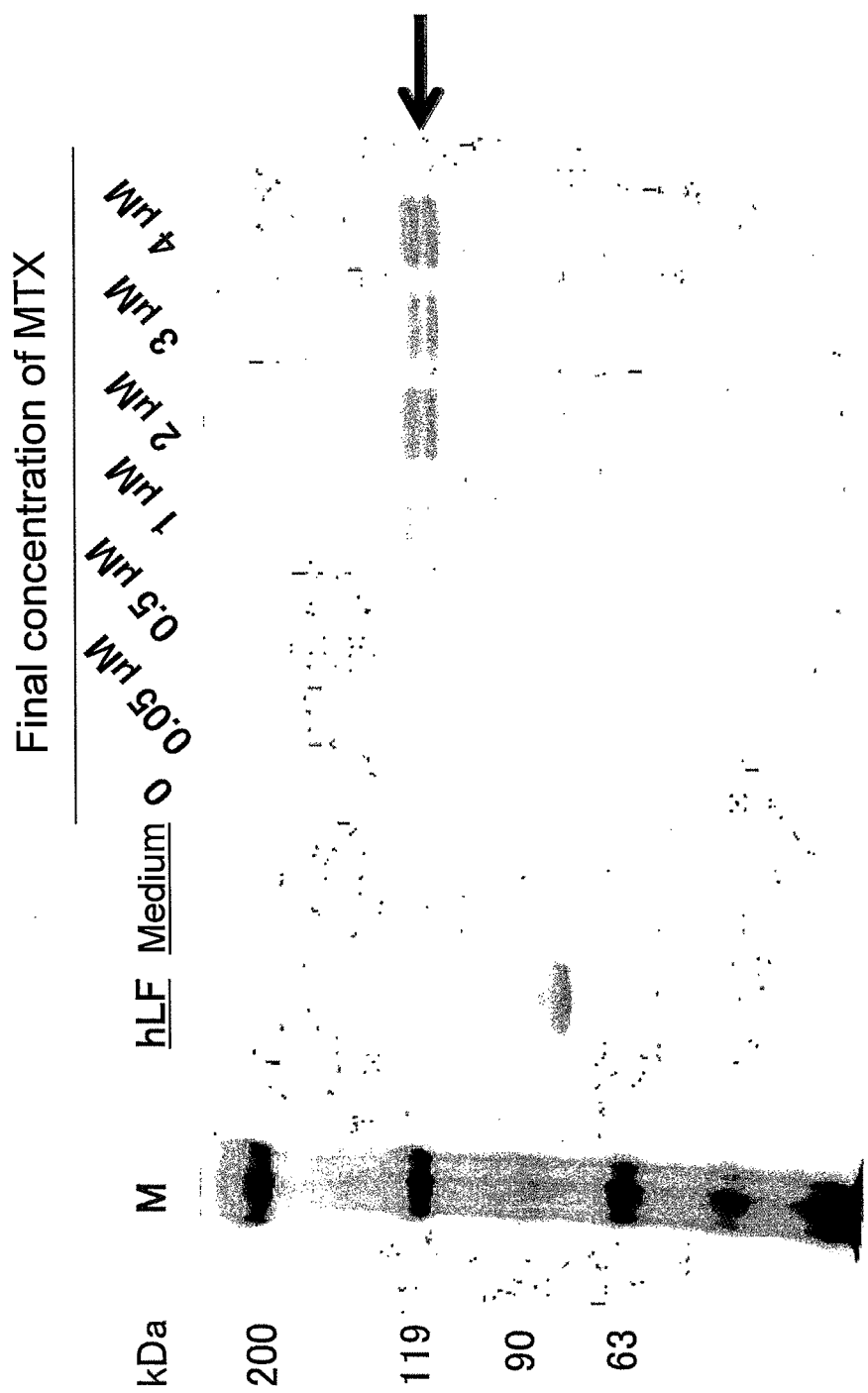
FIG. 7 shows the expression levels obtained when DG44 cells were induced to express the hinge-deficient fusion protein hLF/mhIgGFc.

The results obtained are shown in FIG. 7. The molecular weight of the desired protein hLF/mhIgGFc is approximately 105 kDa. When the MTX concentration reached 0.5 µM, a band was observed around approximately 105 kDa indicated with the arrow. With increase in the MTX concentration, the band was stronger, thus confirming that the expression level of the protein was increased.

The cell line establish in the presence of MTX at a concentration of 4 µM was designated as DG44-hLF/mhIgGFc.

2-3. Large-Scale Expression of the Hinge-Deficient hLF/hIgGFc Fusion Protein

In the same manner as in the case of the hinge-added fusion protein, the cells were subcultured to effect large-scale expression of the fusion protein. The resulting supernatant was stored at 4° C.

2-4. Purification of the Hinge-Deficient hLF/hIgGFc Fusion Protein

In the same manner as in the case of the hinge-added fusion protein, the fusion protein was purified from the culture supernatant obtained by large-scale expression.

Figure 9:
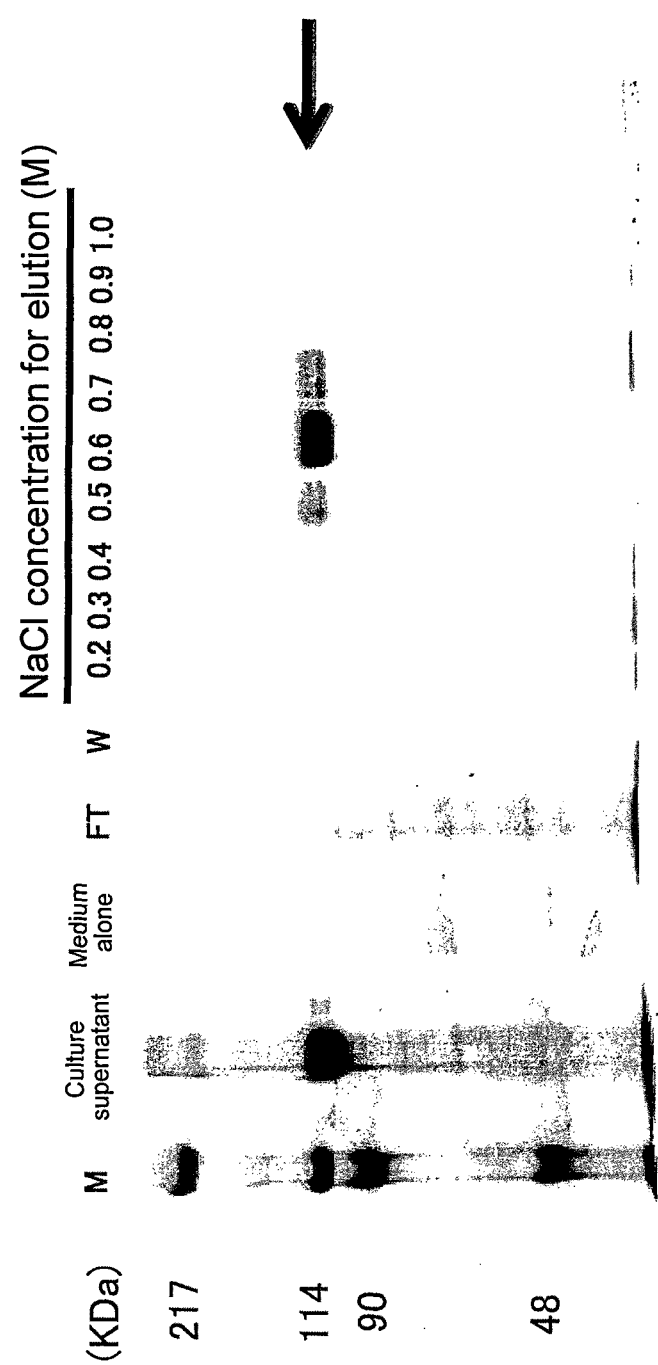
FIG. 9 shows purification of the hinge-deficient fusion protein hLF/mhIgGFc.

The results obtained are shown in FIG. 9. The desired protein hinge-deficient hLF/mhIgGFc was found to be eluted between 0.5 M and 0.7 M NaCl. This result indicated that the hinge-deficient hLF/mhIgGFc bound to "MacroCaP SP" would be able to be efficiently collected in the subsequent cases by being washed with 0.4 M NaCl and eluted with 1.0 M NaCl.

2-5. Concentration of the Hinge-Deficient hLF/hIgGFc Fusion Protein Through Ammonium Sulfate Precipitation In the same manner as in the case of the hinge-added fusion protein, the fusion protein was concentrated through ammonium sulfate precipitation and analyzed by 7.5% SDS-PAGE and CBB staining.

Figure 11:
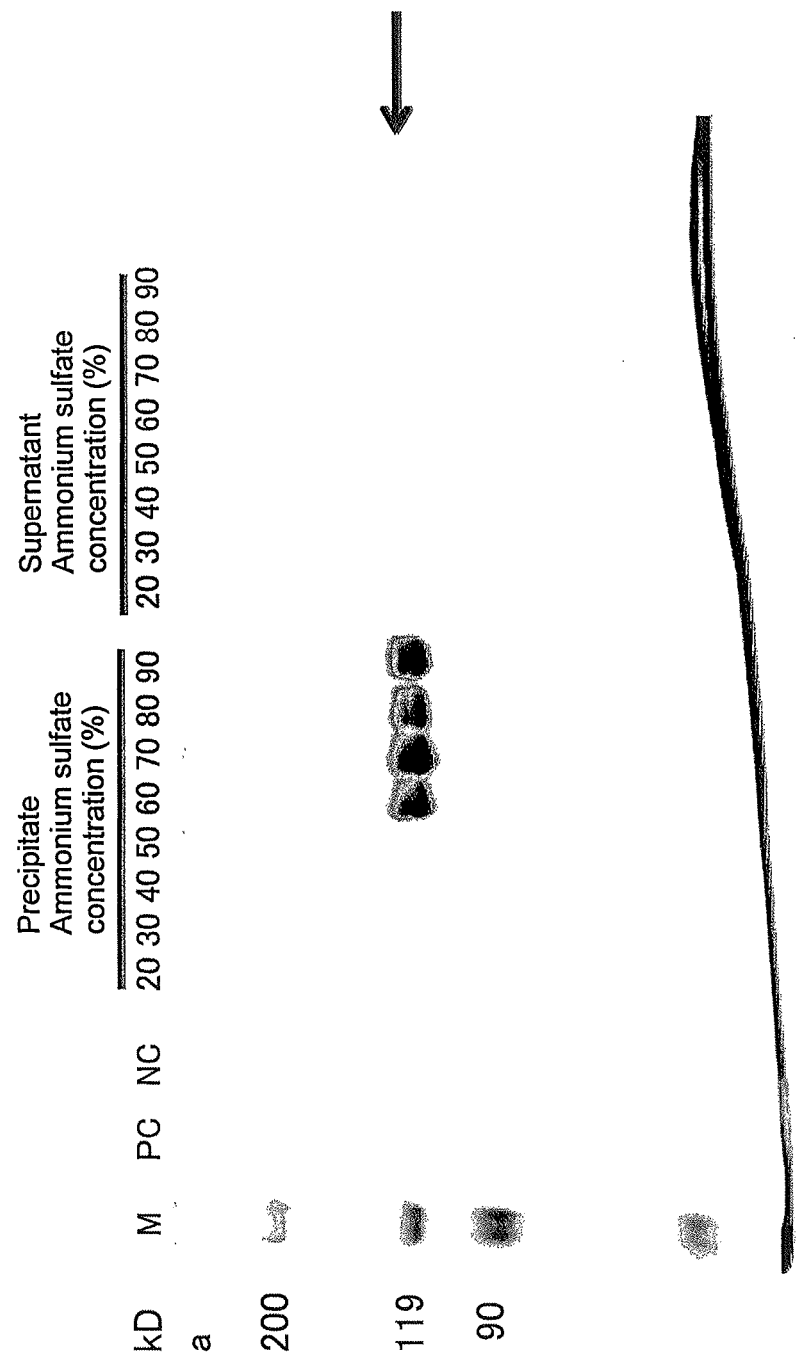
FIG. 11 shows concentration of the hinge-deficient fusion protein hLF/mhIgGFc through ammonium sulfate precipitation.

The results obtained are shown in FIG. 11. Precipitation was observed at 60% to 90% saturation of ammonium sulfate. Further, the fractions showing precipitation at 60% to 90% saturation of ammonium sulfate were measured for their protein concentration in solution by the Bradford assay to calculate the recovery rate in ammonium sulfate precipitation (n=2). Each ammonium sulfate concentration and the recovery rate (%) obtained thereat are shown in Table 5 below.

TABLE 5

| Saturated concentration of ammonium sulfate | Recovery rate (%) |
|---|---|
| 60% | 84.0, 61.7 |
| 70% | 73.4, 58.8 |
| 80% | 71.9, 56.8 |
| 90% | 78.4, 64.2 |

The recovery rate was highest at 60% ammonium sulfate. After ammonium sulfate precipitation, the precipitate was suspended in PBS and dialyzed against PBS to remove ammonium sulfate.

3. Measurement of Biological Activities 3-1. Measurement of the Iron-Binding Ability of the Hinge-Deficient hLF/hIgGFc Fusion Protein The iron-binding ability of lactoferrin was measured in the same manner as in the case of the hinge-added fusion protein. The results of the experiment in duplicate are shown in Table 6 below.

TABLE 6

| | Amount of iron bound per mg of LF (ng) | | | Relative |
|---|---|---|---|---|
| Sample name | Apo form | Holo form | Iron-binding ability (holo form − apo form) | activity (%) |
| (First round) Results measured for iron-binding ability | | | | |
| Recombinant hLF | 154.8 | 1321.0 | 1166.1 | 100 |
| Hinge-deficient fusion protein hLF/mhIgGFc | 147.4 | 1540.0 | 1393.0 | 119 |
| BSA | 54.6 | 167.8 | — | — |

TABLE 6-continued

| Sample name | Amount of iron bound per mg of LF (ng) | | | Relative activity (%) |
| --- | --- | --- | --- | --- |
| | Apo form | Holo form | Iron-binding ability (holo form − apo form) | |
| (Second round) | | | | |
| Recombinant hLF | 220.9 | 1655.5 | 1434.6 | 100 |
| Hinge-deficient fusion protein hLF/mhIgGFc | 275.0 | 1790.0 | 1515.0 | 106 |

Assuming that the iron-binding activity of *Aspergillus*-derived recombinant hLF was set to 100%, the hinge-deficient fusion protein (hLF/mhIgGFc) showed 100% activity.

3-2. CD Spectral Study on the Heat Stability of the Hinge-Deficient hLF/hIgGFc Fusion Protein

*Aspergillus*-derived recombinant hLF and the hinge-added and hinge-deficient hLF/hIgGFc fusion proteins were analyzed for their heat stability by CD spectrometry in the same manner as in the case of the hinge-added fusion protein. The results obtained are shown in FIG. 12. There was no significant difference in secondary structure between the *Aspergillus*-derived recombinant hLF (panel A) and the hinge-deficient hLF/hIgGFc fusion protein (panel B).

Next, each protein was studied for its heat stability in the same manner as in the case of the hinge-added fusion protein. The results obtained are shown in FIG. 13. The *Aspergillus*-derived recombinant hLF (panel A) showed a significant change in its CD spectral values at a temperature around 67° C., whereas the hinge-deficient hLF/hIgGFc fusion protein (panel B) showed no significant change in its CD spectrum at 225 nm even when heated from 30° C. to 90° C.

In view of the foregoing results, when compared to hLF, the hinge-deficient hLF/hIgGFc fusion protein was found to have improved stability against heat and would also be expected to have improved blood stability in vivo.

3-3. Study on the Blood Stability of the Hinge-Deficient hLF/hIgGFc Fusion Protein in Rats Under anesthesia with pentobarbital sodium, a cannula for blood collection was kept in the external jugular vein of each of six Wistar rats (male) at 8 weeks of age. The rats were administered with *Aspergillus*-derived recombinant hLF (at a dose of 1 mg/kg body weight) or the hinge-deficient fusion protein (hLF/mhIgGFc) (at a dose of 1 mg/kg body weight calculated as hLF) by injection into the femoral vein. Before administration and at 5, 10, 15, 30, 60, 120, 180 and 240 minutes after administration, blood was collected through the cannula kept in the external jugular vein, and the hLF concentration in plasma was measured by ELISA ("AssayMax Human Lactoferrin ELISA kit," Assaypro). It should be noted that preliminary studies have been conducted to confirm that the anticoagulant EDTA used during blood collection and plasma do not affect this ELISA measurement. In addition, the ELISA kit used is composed of biotinylated anti-human lactoferrin antibody (primary antibody) and peroxidase-labeled streptavidin. Thus, there is no need for concern about cross-reaction between secondary antibody and hinge-deficient (hLF/mhIgGFc) Fc region, which will cause a problem in commonly used ELISA assays involving the use of secondary antibody.

First, the *Aspergillus*-derived recombinant hLF and the hinge-deficient fusion protein (hLF/mhIgGFc), whose concentration was measured by the Bradford assay, were used to prepare the respective calibration curves. Since linearity was obtained at 0.47 to 7.5 ng/ml for the *Aspergillus*-derived recombinant hLF and at 0.235 to 30.0 ng/ml for the hinge-deficient fusion protein (hLF/mhIgGFc), each plasma sample was diluted such that its measured value fell within this range, and then measured for its protein concentration.

Figure 16:
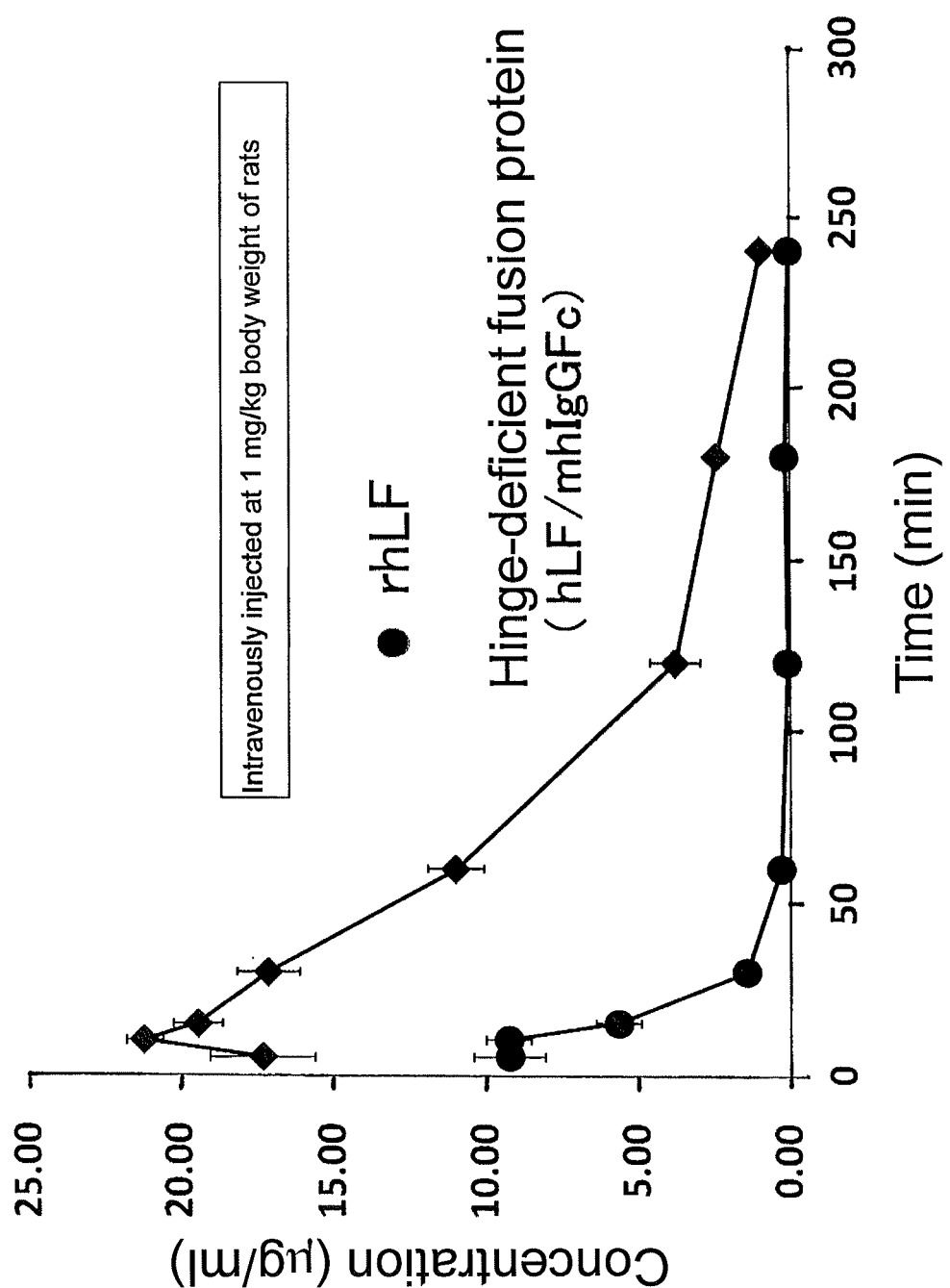
FIG. 16 shows the blood stability of the hinge-deficient fusion protein hLF/mhIgGFc.

The results obtained are shown in FIG. 16. Before administration, LF was not detected from blood in both groups receiving the *Aspergillus*-derived recombinant hLF and the hinge-deficient fusion protein (hLF/mhIgGFc). In the group treated with the *Aspergillus*-derived recombinant hLF, LF was almost cleared from blood at 60 minutes after administration, whereas LF was still detected after 240 minutes in the group treated with the hinge-deficient fusion protein (hLF/mhIgGFc).

Statistical analysis software "GraphPad Prism 4" (GraphPad Software) was used to calculate the half-life in blood and the area under the time curve (AUC). The half-life of hLF in blood of the group treated with the *Aspergillus*-derived recombinant hLF was 12.6 minutes, whereas the half-life of hLF in blood of the group treated with the hinge-deficient fusion protein (hLF/mhIgGFc) was 67.7 minutes, i.e., prolonged about 5.4-fold in the group treated with the hinge-deficient fusion protein (hLF/mhIgGFc). AUC of hLF was increased about 7.4-fold in the group treated with the hinge-deficient fusion protein (hLF/mhIgGFc) in comparison with the group treated with hLF. In view of the foregoing results, when compared to the *Aspergillus*-derived recombinant hLF, the hinge-deficient fusion protein (hLF/mhIgGFc) showed a significant improvement in blood stability.

3-4. In Vitro Protease Resistance Test on the Hinge-Deficient hLF/hIgGFc Fusion Protein In 75% bovine serum/PBS, the hinge-deficient fusion protein (hLF/mhIgGFc) was reacted at a concentration of 0.2 µg/µl for a long period of time at 37° C. After 0, 14, 21, 38 and 55 days, samples were collected and analyzed by immunoblotting with anti-hLF antibody to detect the size and amount of residual LF.

Figure 18:
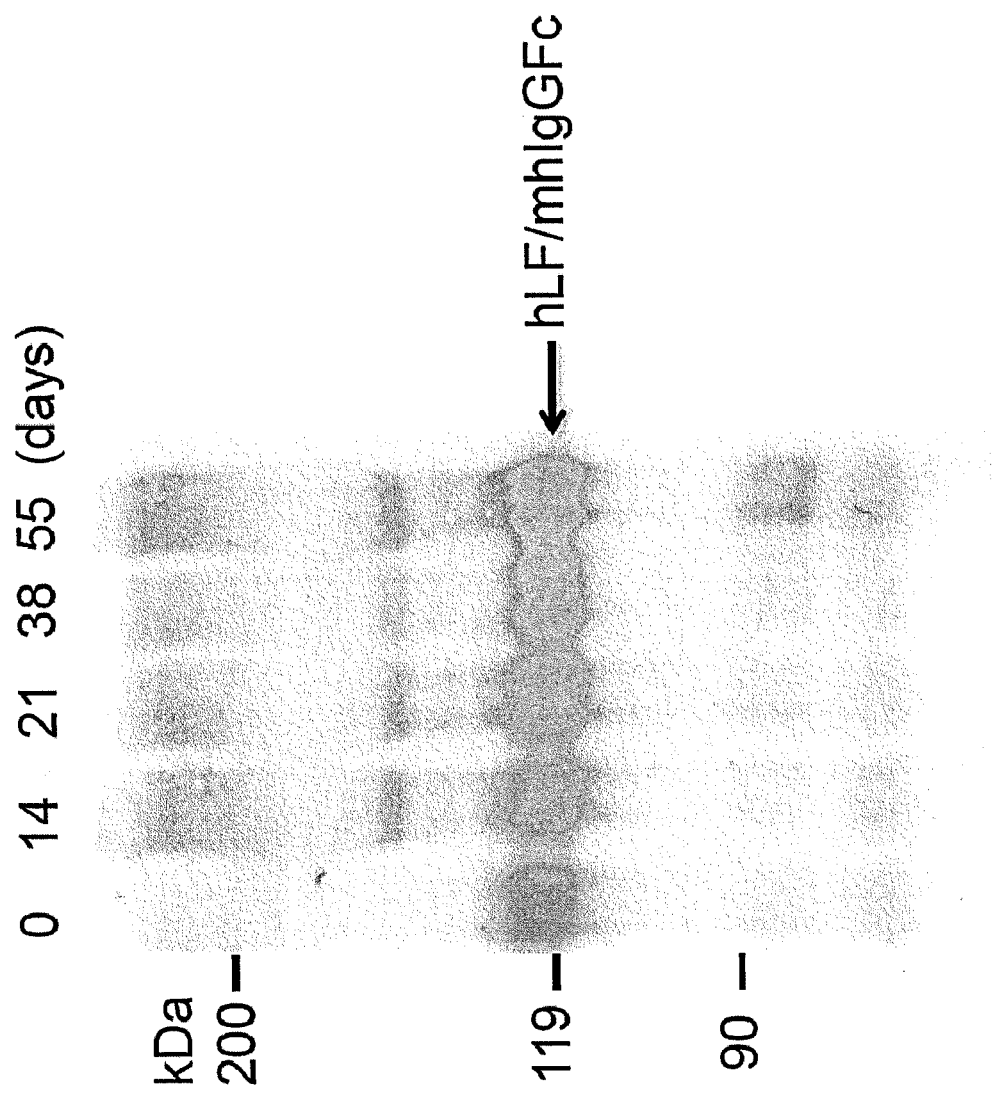
FIG. 18 shows the stability of the hinge-deficient fusion protein hLF/mhIgGFc in a serum solution.

The results indicated that during the storage period up to 55 days, LF received almost no cleavage and hence maintained its initial molecular weight, and also showed no decrease in the amount detected (FIG. 18) when compared to the data obtained at 0 days. Thus, the fusion protein of the present invention has sufficient resistance against protease cleavage in blood.

Example 3: Evaluation of the Fusion Protein ("Hinge-Deficient"), which Formed with Human Lactoferrin and Human IgG Fc Region, for the Uptake into Human Small Intestinal Epithelium-Like Cells and Resistance to Chymotrypsin 1. Evaluation of Uptake into Human Small Intestinal Epithelium-Like Cells (Caco2)

LF is known to be taken up from the intestinal tract and transferred to the thoracic duct lymph. Then, human small intestinal epithelium-like cells (Caco2 cells) were used to confirm whether the hinge-deficient fusion protein (hLF/mhIgGFc) prepared in this study was taken up through this route.

hLF and the hinge-deficient fusion protein (hLF/mhIgGFc) were each labeled with a fluorescent probe, Alexa Fluor 488. To 1 mg of Alexa Fluor 488, 100 µl of DMSO was added. Subsequently, each protein supplemented with 1 M NaHCO$_3$ were mixed with Alexa Fluor 488 at a molar ratio of 1:10 and reacted at room temperature for 1 hour. After the reaction, the reaction solutions were dialyzed against 1×PBS (−) for 24 hours to remove unlabeled Alexa Fluor 488.

Caco-2 cells were seeded in 12-well plates at a cell density of $5\times10^4$ cells/ml and cultured at 37° C. in 5% $CO_2$ for 1 week (with medium replacement every 2 days). To the Caco-2 cells, PBS(−) was added at 1 ml/well, and washing was repeated three times for complete removal of the medium components. Next, each protein labeled with Alexa was added at 15 μg/well and reacted for 1 hour. After 1 hour, each protein labeled with Alexa was removed, and the cells were washed once by addition of cold PBS(−) at 1 ml/well. After washing, 0.25% Trypsin/EDTA was added at 250 μl/well and reacted under conditions of 37° C. for 5 minutes. After 5 minutes, all the cells were collected into tubes and centrifuged at 200×g for 2 minutes at 4° C. using a centrifuge. After centrifugation, the supernatants were removed and cold PBS(−) was added at 1 ml/tube to lightly suspend the cells, followed by centrifugation at 200×g for 2 minutes at 4° C. After centrifugation, the supernatants were removed and 4% PFA/PBS(−) was added at 200 μl/tube to lightly suspend the cells, followed by reaction at room temperature for 15 minutes. After 15 minutes, the tubes were centrifuged at 200×g for 2 minutes at 4° C. After centrifugation, the supernatants were removed and 1 μg/ml bisbenzimide/PBS (−) was added at 200 μl/tube to lightly suspend the cells, followed by reaction at room temperature for 15 minutes (nuclear staining). After 15 minutes, the tubes were centrifuged at 200×g for 2 minutes at 4° C. After centrifugation, the supernatants were removed and cold PBS(−) was added at 200 μl/tube to lightly suspend the cells. After suspension, the tubes were centrifuged at 200×g for 2 minutes at 4° C. After centrifugation, the supernatants were removed and cold PBS(−) was added at 200 μl/tube to lightly suspend the cells, followed by transferring the suspensions in their entirety to a 8-well chamber plate. Then, fluorescence uptake was observed with a confocal laser scanning microscope LSM510.

Figure 19:
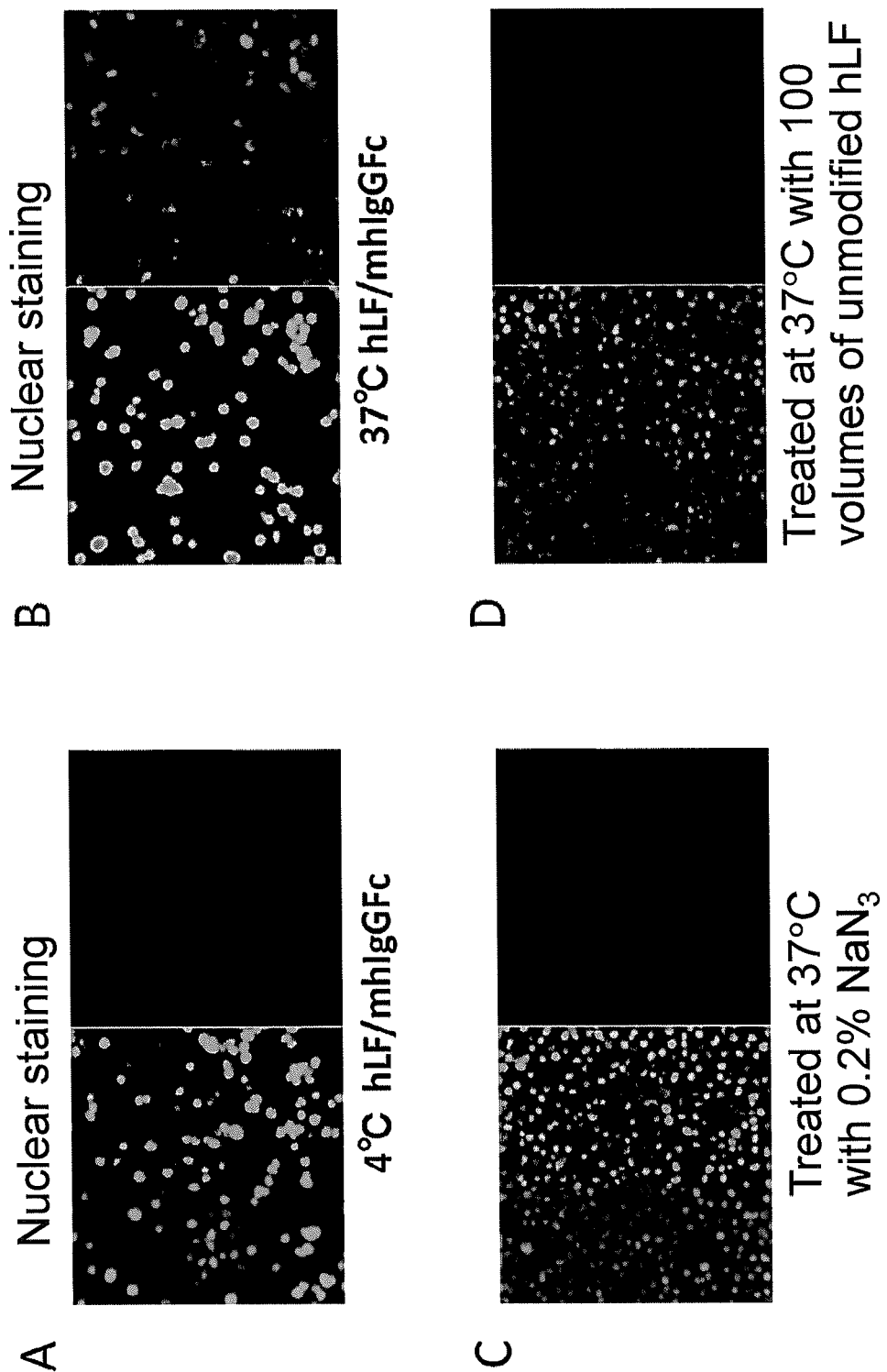
FIG. 19 shows the uptake of the hinge-deficient fusion protein hLF/mhIgGFc into small intestinal epithelium-like cells.

As a result, hLF and the hinge-deficient fusion protein (hLF/mhIgGFc) were confirmed not to be taken up into Caco2 cells under conditions of 4° C. (FIG. 19A), but to be taken up into Caco2 cells under conditions of 37° C. (FIG. 19B). Moreover, their uptake at 37° C. was inhibited in the presence of $NaN_3$ (FIG. 19C) and an excessive amount of unlabeled bovine lactoferrin (bLF) (FIG. 19D), thus confirming that this intracellular uptake was receptor-mediated and the hinge-deficient fusion protein (hLF/mhIgGFc) was taken up into cells through the same uptake route as LF. Namely, the hinge-deficient fusion protein (hLF/mhIgGFc) is considered to be taken up via any one or more of the lactoferrin receptor, the IgG receptor or the albumin receptor.

2. Evaluation of Chymotrypsin Digestion Resistance in the Hinge-Deficient Fusion Protein (hLF/mhIgGFc)

The buffer used in this experiment was prepared as indicated in Table 7 and then adjusted to pH 7.4.

TABLE 7

Table 7 Composition of buffer

| | |
|---|---|
| 1M Tris-HCl (pH 8.8) | 2.5 ml |
| 5M NaCl | 1 ml |
| 1M $CaCl_2 \cdot 2H_2O$ | 100 μl |
| Mess up to | 50 ml | hLF and the hinge-deficient fusion protein (hLF/mhIgGFc) were suspended at 1 mg/ml in this buffer.

[Digestive Enzyme Resistance Test]

150 μl of 1 mg/ml hLF or hinge-deficient fusion protein (hLF/mhIgGFc) was mixed with 120 μl of the buffer and allowed to stand at 37° C. for 5 minutes. Then, a 16.7 μg/ml chymotrypsin solution (30 μl) was added to reaction samples and reacted by being allowed to stand at 37° C. Reaction samples (36 μl each) were collected over time and each added to 12 μl of Sample Buffer prepared in advance (0.1 M Tris-HCl (pH 6.8), 4% SDS, 20% glycerol, a trace amount of BPB) to stop the digestion reaction. Then, the reaction solutions were electrophoresed by 10% SDS-PAGE (each solution was used at 15 μl/lane), followed by CBB staining.

Figure 20:
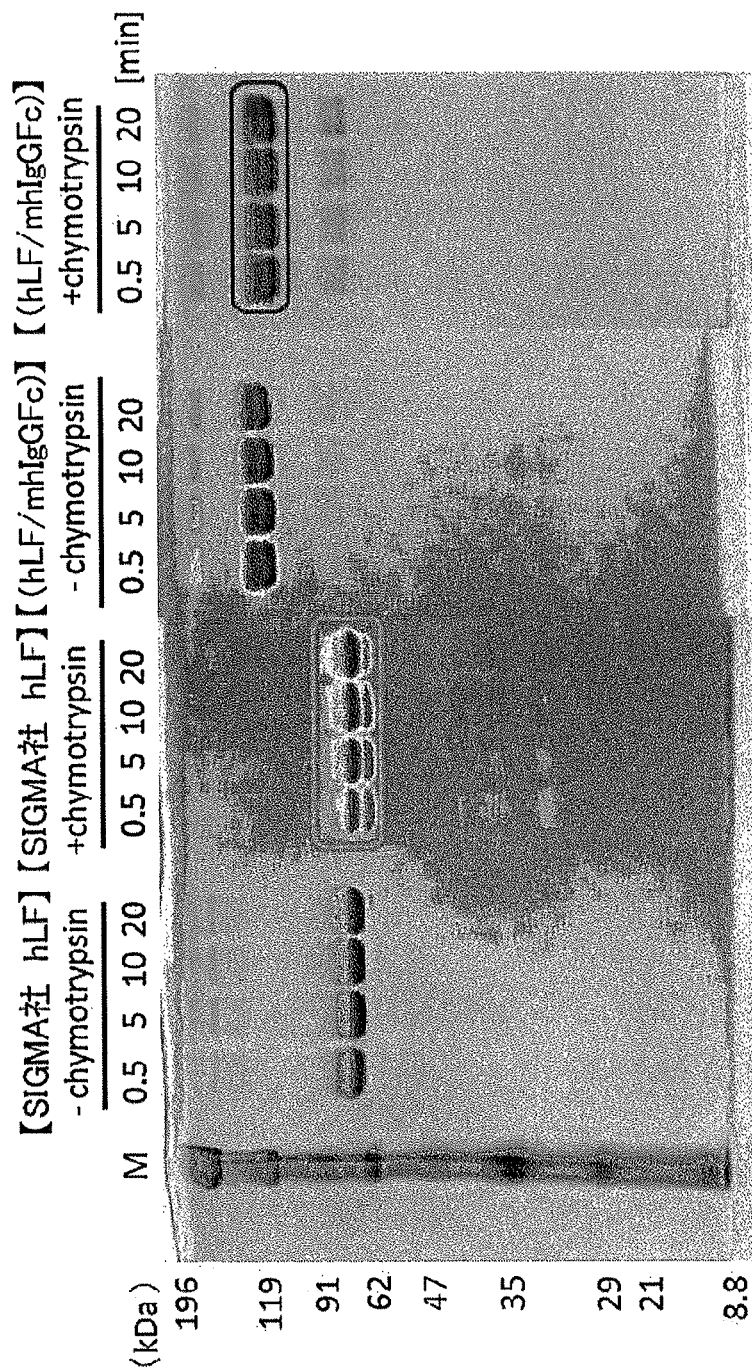
FIG. 20 is an electrophoresis photograph showing the chymotrypsin resistance of the hinge-deficient fusion protein hLF/mhIgGFc.

FIG. 20 shows the results of electrophoresis obtained for, from the left, a molecular weight marker, hLF samples allowed to stand at 37° C. in the absence of chymotrypsin, hLF samples allowed to stand at 37° C. in the presence of chymotrypsin, hinge-deficient fusion protein (hLF/mhIgGFc) samples allowed to stand at 37° C. in the absence of chymotrypsin, and hinge-deficient fusion protein (hLF/mhIgGFc) samples allowed to stand at 37° C. in the presence of chymotrypsin.

Figure 21:
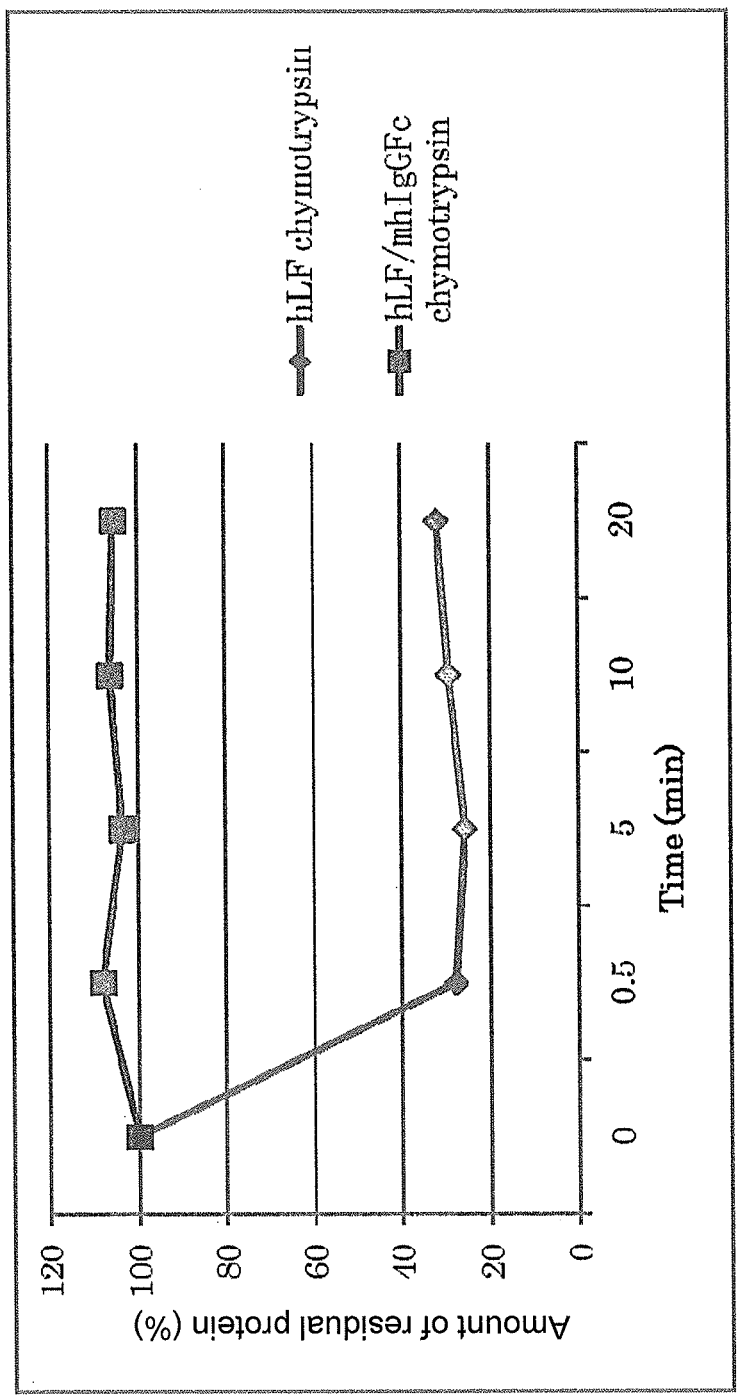
FIG. 21 shows the chymotrypsin resistance of the hinge-deficient fusion protein hLF/mhIgGFc.

The density of each band was analyzed by ImageJ. The results were plotted on a graph, assuming that the mean density of the band in the absence of chymotrypsin was set to 100% (FIG. 21). The hinge-deficient fusion protein (hLF/mhIgGFc) was almost not cleaved, whereas hLF serving as a control was cleaved within 30 seconds, thus indicating that the hinge-deficient fusion protein (hLF/mhIgGFc) was resistant to chymotrypsin digestion.

Figure 22:
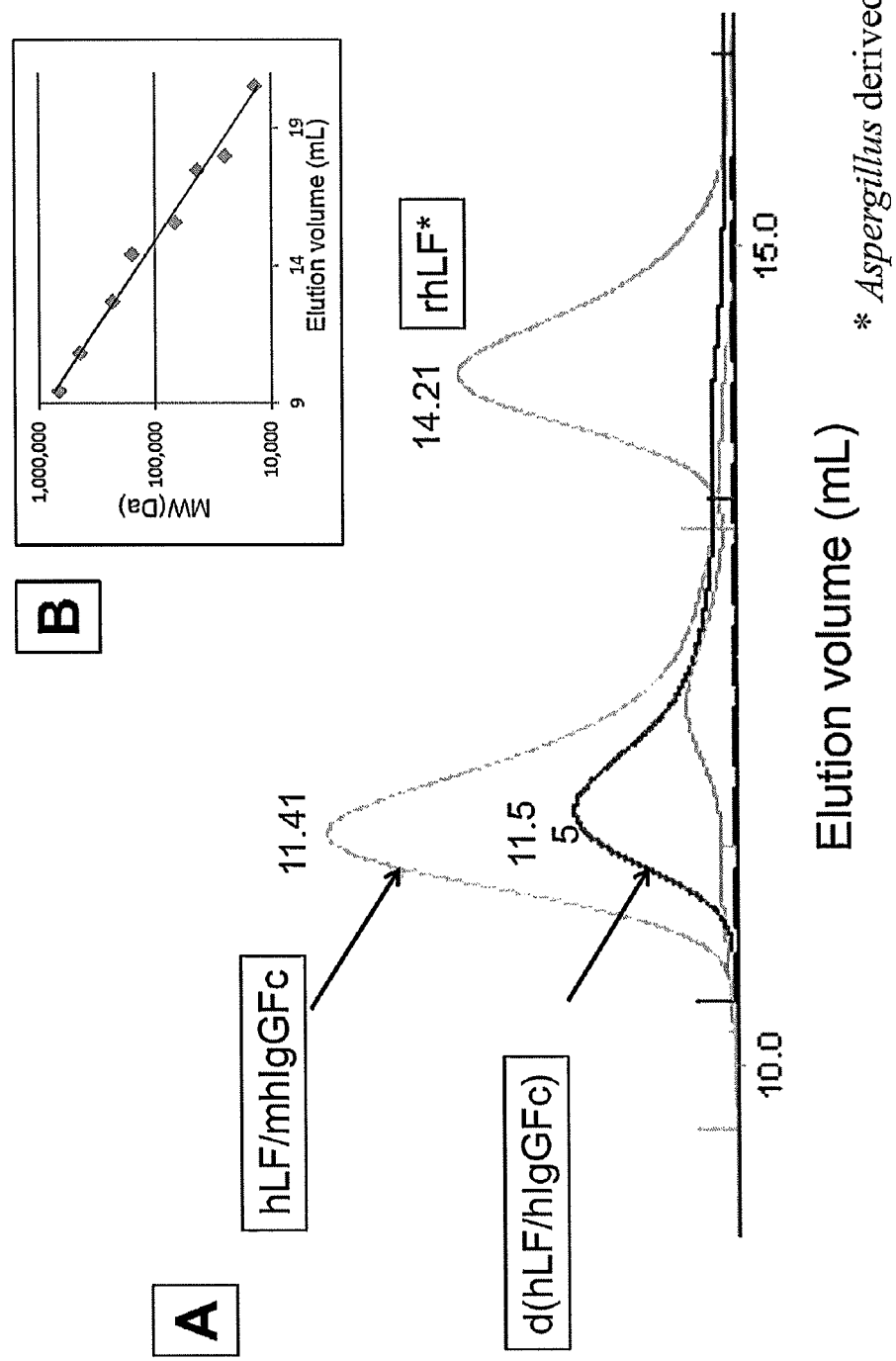
FIG. 22 shows homodimer formation in a solution from the hinge-deficient fusion protein hLF/mhIgGFc.

In addition, hLF and the hinge-deficient fusion protein (hLF/mhIgGFc), each being dissolved in the buffer indicated in Table 7, were analyzed by gel column chromatography, indicating that the hinge-deficient fusion protein (hLF/mhIgGFc) was present as a homodimer (FIG. 22).

Panel B in FIG. 22 is a graph showing the correlation between elution time and protein molecular weight. In the chromatograph (FIG. 22, panel A), the blue curve ("hLF/dhIgGFc") represents the results of the hinge-added hLF/hIgGFc fusion protein containing the region for dimer formation (i.e., the hinge region). On the other hand, the green curve ("hLF/mhIgGFc") represents the results of the hinge-deficient fusion protein (hLF/mhIgGFc). Gel filtration of hLF/mhIgGFc and hLF/dhIgGFc indicated that there was almost no difference in their elution time. This suggested that the hinge-deficient fusion protein (hLF/mhIgGFc) would form a dimer in a solution.

INDUSTRIAL APPLICABILITY

The present invention provides a lactoferrin fusion protein having improved properties, uses thereof and a method for preparation thereof.

The invention claimed is:

1. A fusion protein comprising the amino acid sequence of SEQ ID NO: 5 or 6.

2. A nucleic acid molecule encoding the fusion protein according to claim 1.

3. An expression vector comprising the nucleic acid molecule: according to claim 2.

4. An isolated host cell comprising the expression vector according to claim 3.

5. A pharmaceutical composition comprising the fusion protein according to claim 1 and a carrier.

6. A method for preparing a fusion protein, which comprises culturing a host cell comprising the nucleic acid molecule of claim 2 in a medium to express the fusion protein, and collecting the fusion protein from the host cell or the medium.

* * * * *